(12) United States Patent
Chang et al.

(10) Patent No.: US 8,986,955 B2
(45) Date of Patent: Mar. 24, 2015

(54) METHOD FOR INCREASING THERMAL STABILITY AND RETAINING ACTIVITY OF A PROTEIN

(71) Applicant: Simpson Biotech Co., Ltd., Taoyuan County (TW)

(72) Inventors: Margaret Dah-Tsyr Chang, Hsinchu (TW); Chia-Chin Sheu, Taoyuan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 13/646,996

(22) Filed: Oct. 8, 2012

(65) Prior Publication Data

US 2013/0034877 A1  Feb. 7, 2013

Related U.S. Application Data

(63) Continuation-in-part of application No. 12/777,308, filed on May 11, 2010.

(60) Provisional application No. 61/178,816, filed on May 15, 2009.

(51) Int. Cl.
| | |
|---|---|
| *C12P 23/00* | (2006.01) |
| *C07K 1/22* | (2006.01) |
| *C07K 1/32* | (2006.01) |
| *C12N 9/02* | (2006.01) |
| *C12N 9/16* | (2006.01) |
| *C12N 9/20* | (2006.01) |
| *C12N 9/42* | (2006.01) |
| *C12N 9/50* | (2006.01) |
| *C12N 11/10* | (2006.01) |
| *C12N 9/96* | (2006.01) |

(52) U.S. Cl.
CPC ... *C07K 1/22* (2013.01); *C07K 1/32* (2013.01); *C07K 2319/20* (2013.01); *C12N 9/0004* (2013.01); *C12N 9/16* (2013.01); *C12N 9/20* (2013.01); *C12N 9/2434* (2013.01); *C12N 9/2437* (2013.01); *C12N 9/50* (2013.01); *C12N 11/10* (2013.01); *C12N 9/96* (2013.01)
USPC ......................................... 435/69.7; 435/178

(58) Field of Classification Search
CPC ............. C12N 9/2437; C12N 15/1086; C12N 15/1034; C12N 15/635; C12N 15/70; C12N 15/80; C12N 15/81; C12N 15/8216; C12N 15/8218; C12N 15/8261; C12N 15/8266; C12N 15/8271; C12N 9/2402; C12N 9/2428; C12N 9/52
USPC .................................................. 435/69.7, 178
See application file for complete search history.

(56) References Cited

U.S. PATENT DOCUMENTS

| | | | |
|---|---|---|---|
| 7,851,215 B2 * | 12/2010 | Chang et al. | 435/320.1 |
| 2006/0270007 A1 * | 11/2006 | Nielsen et al. | 435/101 |
| 2007/0134375 A1 * | 6/2007 | Habich et al. | 426/53 |

OTHER PUBLICATIONS

Xue et al., J, Gen. Appl. Microbiol. Functional expression of LZ-8, a fungal immunoregulatory protein from *Ganoderma lucidium* in *Pichia pastoris*. 54, 393 398, 2008.*
Kuo et al., Engineering a novel endopeptidase based on SARS 3CLpro. Biotechniques, 47 (6), 1029-1032, 2009.*
Hearn et al., Applications of novel affinity cassette methods: use of peptide fusion handles for the purification of recombinant proteins. J. Mol. Recognit. 14: 323-369, 2001.*
Xue et al., J, Gen. Appl. Microbiol. Functional expression of LZ- 8, a fungal immunoregulatory protein from *Ganoderma lucidium* in *Pichia pastoris*. 54, 393 398, 2008.*
Kuo et al., Engineering a novel endopeptidase based on SARS 3CLpro. Biotechniques, 47 (6), 1029-1032, 2009,.*
Boraston et al., Methods for Affinity-Based Separations of Enzymes and Proteins, ed. by Munishwar N. Gupta; Birkhiiuser Verlag BaseVSwitzerland, 2002.*

* cited by examiner

*Primary Examiner* — Tekchand Saidha
(74) *Attorney, Agent, or Firm* — Hannah M. Tien

(57) ABSTRACT

The present invention provides a method and a system for increasing thermal stability of a target protein comprising fusing a starch binding protein (SBP) with the target protein to form a SBP-tagged recombinant protein and combining the SBP-tagged recombinant protein with a SBP-binding matrix. The present invention also provides a method for retaining an activity of a target protein in aquatic environment comprising fusing a starch binding protein (SBP) with the target protein to form a SBP-tagged recombinant protein and combining the SBP-tagged recombinant protein with a SBP-binding matrix.

7 Claims, 11 Drawing Sheets

M: marker

In: input

P: starch pellet after binding (bound protein)

S: supernatant after binding (unbound protein)

M: marker

In: input

P: starch pellet after binding (bound protein)

S: supernatant after binding (unbound protein)

M: marker

In: input

S: supernatant after binding (unbound protein)

E: eluent

M: marker

S: serum

FT: flowthrough

W: washing solution

E: eluent

SEQUENCE LISTING

```
<160> NUMBER OF SEQ ID NOS: 15

<210> SEQ ID NO 1
<211> LENGTH: 318
<212> TYPE: DNA
<213> ORGANISM: Rhizopus oryzae
<220> FEATURE:
<221> NAME/KEY: CDS
<222> LOCATION: (1)..(318)

<400> SEQUENCE: 1 gca agt att cct agc agt gct tct gtc cag ctt gat tca tac aac tac      48
Ala Ser Ile Pro Ser Ser Ala Ser Val Gln Leu Asp Ser Tyr Asn Tyr
1               5                   10                  15 gat ggc tct act ttt tca gga aaa att tat gtc aag aac att gct tac      96
Asp Gly Ser Thr Phe Ser Gly Lys Ile Tyr Val Lys Asn Ile Ala Tyr
            20                  25                  30 tcc aag aaa gtt act gta gtc tac gcc gat ggc tct gac aac tgg aat     144
Ser Lys Lys Val Thr Val Val Tyr Ala Asp Gly Ser Asp Asn Trp Asn
        35                  40                  45 aat aat gga aac atc att gct gct tct ttc tct ggc cct atc tct gga     192
Asn Asn Gly Asn Ile Ile Ala Ala Ser Phe Ser Gly Pro Ile Ser Gly
    50                  55                  60 tca aat tac gaa tac tgg aca ttc tct gcc tcc gtt aaa ggt atc aag     240
Ser Asn Tyr Glu Tyr Trp Thr Phe Ser Ala Ser Val Lys Gly Ile Lys
65                  70                  75                  80 gag ttc tac att aag tat gaa gtc agt gga aaa aca tac tat gat aac     288
Glu Phe Tyr Ile Lys Tyr Glu Val Ser Gly Lys Thr Tyr Tyr Asp Asn
                85                  90                  95 aac aat tct gcc aat tac caa gta tct aca                             318
Asn Asn Ser Ala Asn Tyr Gln Val Ser Thr
            100                 105

<210> SEQ ID NO 2
<211> LENGTH: 106
<212> TYPE: PRT
<213> ORGANISM: Rhizopus oryzae

<400> SEQUENCE: 2

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30
```

```
Ser Lys Lys Val Thr Val Tyr Ala Asp Gly Ser Asp Asn Trp Asn
        35                  40                  45

Asn Asn Gly Asn Ile Ile Ala Ser Phe Ser Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr
            100                 105

<210> SEQ ID NO 3
<211> LENGTH: 1179
<212> TYPE: DNA
<213> ORGANISM: Rhizopus oryzae
<220> FEATURE:
<221> NAME/KEY: CDS
<222> LOCATION: (1)..(1179)

<400> SEQUENCE: 3
```

| | | | | | | | | | | | | | | | | |
|---|---|---|---|---|---|---|---|---|---|---|---|---|---|---|---|---|
| atg | gtt | tca | ttt | att | tcc | att | tct | caa | ggt | gtt | agt | ctt | tgt | ctt | ctt | 48 |
| Met | Val | Ser | Phe | Ile | Ser | Ile | Ser | Gln | Gly | Val | Ser | Leu | Cys | Leu | Leu | |
| 1 | | | | 5 | | | | | 10 | | | | | 15 | | |
| gtc | tct | tcc | atg | atg | ctc | ggt | tca | tct | gct | gtt | cct | gtt | tct | ggt | aaa | 96 |
| Val | Ser | Ser | Met | Met | Leu | Gly | Ser | Ser | Ala | Val | Pro | Val | Ser | Gly | Lys | |
| | | | | 20 | | | | | 25 | | | | | 30 | | |
| tct | gga | tct | tcc | aac | acc | gcc | gtc | tct | gca | tct | gac | aat | gct | gcc | ctc | 144 |
| Ser | Gly | Ser | Ser | Asn | Thr | Ala | Val | Ser | Ala | Ser | Asp | Asn | Ala | Ala | Leu | |
| | | 35 | | | | | 40 | | | | | 45 | | | | |
| cct | cct | ctc | atc | tcc | agc | cgt | tgt | gct | cct | cct | tct | aac | aag | gga | agt | 192 |
| Pro | Pro | Leu | Ile | Ser | Ser | Arg | Cys | Ala | Pro | Pro | Ser | Asn | Lys | Gly | Ser | |
| | | 50 | | | | | 55 | | | | | 60 | | | | |
| aaa | agc | gat | ctc | caa | gct | gaa | cct | tac | aac | atg | caa | aag | aat | aca | gaa | 240 |
| Lys | Ser | Asp | Leu | Gln | Ala | Glu | Pro | Tyr | Asn | Met | Gln | Lys | Asn | Thr | Glu | |
| 65 | | | | | 70 | | | | | 75 | | | | | 80 | |
| tgg | tat | gag | tct | cat | ggt | ggc | aac | ctg | aca | tcc | atc | gga | aag | cgt | gat | 288 |
| Trp | Tyr | Glu | Ser | His | Gly | Gly | Asn | Leu | Thr | Ser | Ile | Gly | Lys | Arg | Asp | |
| | | | | 85 | | | | | 90 | | | | | 95 | | |
| gac | aac | ttg | gtt | ggt | ggc | atg | act | ttg | gac | tta | ccc | agc | gat | gct | cct | 336 |
| Asp | Asn | Leu | Val | Gly | Gly | Met | Thr | Leu | Asp | Leu | Pro | Ser | Asp | Ala | Pro | |
| | | | | 100 | | | | | 105 | | | | | 110 | | |
| cct | atc | ggc | ctc | tct | agc | tct | acc | aac | agc | gcc | ttt | gat | ggt | ggt | aag | 384 |
| Pro | Ile | Gly | Leu | Ser | Ser | Ser | Thr | Asn | Ser | Ala | Phe | Asp | Gly | Gly | Lys | |
| | | | | 115 | | | | | 120 | | | | | 125 | | |
| gtt | gtt | gct | gct | act | act | gct | cag | atc | caa | gag | ttc | acc | aag | tat | gct | 432 |
| Val | Val | Ala | Ala | Thr | Thr | Ala | Gln | Ile | Gln | Glu | Phe | Thr | Lys | Tyr | Ala | |
| | | | 130 | | | | | 135 | | | | | 140 | | | |
| ggt | atc | gct | gcc | act | gct | tac | tgt | cgt | tct | gtt | gtc | cct | ggt | aac | aag | 480 |
| Gly | Ile | Ala | Ala | Thr | Ala | Tyr | Cys | Arg | Ser | Val | Val | Pro | Gly | Asn | Lys | |
| 145 | | | | | 150 | | | | | 155 | | | | | 160 | |
| tgg | gat | tgt | gtc | caa | tgt | caa | aag | tgg | gtt | cct | gat | ggc | aag | atc | atc | 528 |
| Trp | Asp | Cys | Val | Gln | Cys | Gln | Lys | Trp | Val | Pro | Asp | Gly | Lys | Ile | Ile | |
| | | | | 165 | | | | | 170 | | | | | 175 | | |
| act | acc | ttt | acc | tcc | ttg | ctt | tcc | gat | aca | aat | ggt | tac | gtc | ttg | aga | 576 |
| Thr | Thr | Phe | Thr | Ser | Leu | Leu | Ser | Asp | Thr | Asn | Gly | Tyr | Val | Leu | Arg | |
| | | | | 180 | | | | | 185 | | | | | 190 | | |
| agt | gat | aaa | caa | aag | acc | att | tat | ctt | gtt | ttc | cgt | ggt | acc | aac | tcc | 624 |
| Ser | Asp | Lys | Gln | Lys | Thr | Ile | Tyr | Leu | Val | Phe | Arg | Gly | Thr | Asn | Ser | |
| | | | | 195 | | | | | 200 | | | | | 205 | | |

```
ttc aga agt gcc atc act gat att gtc ttc aac ttt tct gac tac aag    672
Phe Arg Ser Ala Ile Thr Asp Ile Val Phe Asn Phe Ser Asp Tyr Lys
    210             215                 220 cct gtc aag ggc gcc aaa gtt cat gct ggt ttc ctt tcc tct tat gag    720
Pro Val Lys Gly Ala Lys Val His Ala Gly Phe Leu Ser Ser Tyr Glu
225             230                 235                 240 caa gtt gtc aat gac tat ttc cct gtc gtc caa gaa caa ttg acc gcc    768
Gln Val Val Asn Asp Tyr Phe Pro Val Val Gln Glu Gln Leu Thr Ala
                245                 250                 255 cac cct act tat aag gtc atc gtt acc ggt cac tca ctc ggt ggt gca    816
His Pro Thr Tyr Lys Val Ile Val Thr Gly His Ser Leu Gly Gly Ala
            260                 265                 270 caa gct ttg ctt gcc ggt atg gat ctc tac caa cgt gaa cca aga ttg    864
Gln Ala Leu Leu Ala Gly Met Asp Leu Tyr Gln Arg Glu Pro Arg Leu
        275                 280                 285 tct ccc aag aat ttg agc atc ttc act gtc ggt ggt cct cgt gtt ggt    912
Ser Pro Lys Asn Leu Ser Ile Phe Thr Val Gly Gly Pro Arg Val Gly
    290                 295                 300 aac ccc gcc ttt gct tac tat gtt gaa tcc acc ggt atc cct ttc caa    960
Asn Pro Ala Phe Ala Tyr Tyr Val Glu Ser Thr Gly Ile Pro Phe Gln
305                 310                 315                 320 cgt acc gtt cac aag aga gat atc gtt cct cac gtt cct cct caa tcc   1008
Arg Thr Val His Lys Arg Asp Ile Val Pro His Val Pro Pro Gln Ser
                325                 330                 335 ttc gga ttc ctt cat ccc ggt gtt gaa tct tgg atc aag tct ggt act   1056
Phe Gly Phe Leu His Pro Gly Val Glu Ser Trp Ile Lys Ser Gly Thr
            340                 345                 350 tcc aac gtt caa atc tgt act tct gaa att gaa acc aag gat tgc agt   1104
Ser Asn Val Gln Ile Cys Thr Ser Glu Ile Glu Thr Lys Asp Cys Ser
        355                 360                 365 aac tct atc gtt cct ttc acc tct atc ctt gac cac ttg agt tac ttt   1152
Asn Ser Ile Val Pro Phe Thr Ser Ile Leu Asp His Leu Ser Tyr Phe
    370                 375                 380 gat atc aac gaa gga agc tgt ttg taa                                1179
Asp Ile Asn Glu Gly Ser Cys Leu
385                 390

<210> SEQ ID NO 4
<211> LENGTH: 392
<212> TYPE: PRT
<213> ORGANISM: Rhizopus oryzae

<400> SEQUENCE: 4

Met Val Ser Phe Ile Ser Ile Ser Gln Gly Val Ser Leu Cys Leu Leu
1               5                   10                  15

Val Ser Ser Met Met Leu Gly Ser Ser Ala Val Pro Val Ser Gly Lys
            20                  25                  30

Ser Gly Ser Ser Asn Thr Ala Val Ser Ala Ser Asp Asn Ala Ala Leu
        35                  40                  45

Pro Pro Leu Ile Ser Ser Arg Cys Ala Pro Ser Asn Lys Gly Ser
    50                  55                  60

Lys Ser Asp Leu Gln Ala Glu Pro Tyr Asn Met Gln Lys Asn Thr Glu
65                  70                  75                  80

Trp Tyr Glu Ser His Gly Gly Asn Leu Thr Ser Ile Gly Lys Arg Asp
                85                  90                  95

Asp Asn Leu Val Gly Gly Met Thr Leu Asp Leu Pro Ser Asp Ala Pro
            100                 105                 110

Pro Ile Gly Leu Ser Ser Ser Thr Asn Ser Ala Phe Asp Gly Gly Lys
        115                 120                 125
```

```
Val Val Ala Ala Thr Thr Ala Gln Ile Gln Glu Phe Thr Lys Tyr Ala
    130                 135                 140
Gly Ile Ala Ala Thr Ala Tyr Cys Arg Ser Val Val Pro Gly Asn Lys
145                 150                 155                 160
Trp Asp Cys Val Gln Cys Gln Lys Trp Val Pro Asp Gly Lys Ile Ile
                165                 170                 175
Thr Thr Phe Thr Ser Leu Leu Ser Asp Thr Asn Gly Tyr Val Leu Arg
            180                 185                 190
Ser Asp Lys Gln Lys Thr Ile Tyr Leu Val Phe Arg Gly Thr Asn Ser
        195                 200                 205
Phe Arg Ser Ala Ile Thr Asp Ile Val Phe Asn Phe Ser Asp Tyr Lys
    210                 215                 220
Pro Val Lys Gly Ala Lys Val His Ala Gly Phe Leu Ser Ser Tyr Glu
225                 230                 235                 240
Gln Val Val Asn Asp Tyr Phe Pro Val Gln Glu Gln Leu Thr Ala
                245                 250                 255
His Pro Thr Tyr Lys Val Ile Val Thr Gly His Ser Leu Gly Gly Ala
            260                 265                 270
Gln Ala Leu Leu Ala Gly Met Asp Leu Tyr Gln Arg Glu Pro Arg Leu
        275                 280                 285
Ser Pro Lys Asn Leu Ser Ile Phe Thr Val Gly Gly Pro Arg Val Gly
    290                 295                 300
Asn Pro Ala Phe Ala Tyr Tyr Val Glu Ser Thr Gly Ile Pro Phe Gln
305                 310                 315                 320
Arg Thr Val His Lys Arg Asp Ile Val Pro His Val Pro Gln Ser
                325                 330                 335
Phe Gly Phe Leu His Pro Gly Val Glu Ser Trp Ile Lys Ser Gly Thr
            340                 345                 350
Ser Asn Val Gln Ile Cys Thr Ser Glu Ile Glu Thr Lys Asp Cys Ser
        355                 360                 365
Asn Ser Ile Val Pro Phe Thr Ser Ile Leu Asp His Leu Ser Tyr Phe
    370                 375                 380
Asp Ile Asn Glu Gly Ser Cys Leu
385                 390

<210> SEQ ID NO 5
<211> LENGTH: 906
<212> TYPE: DNA
<213> ORGANISM: Neocallimastix frontalis
<220> FEATURE:
<221> NAME/KEY: CDS
<222> LOCATION: (1)..(906)

<400> SEQUENCE: 5 ccg tta act gtt gct aag gcc caa tgg ggt aga ggt gct tcc gct ggt      48
Pro Leu Thr Val Ala Lys Ala Gln Trp Gly Arg Gly Ala Ser Ala Gly
1               5                   10                  15 caa aaa ttg tcc gtc ggt ggt ggt caa aac caa cat aag ggt gtc tcc      96
Gln Lys Leu Ser Val Gly Gly Gly Gln Asn Gln His Lys Gly Val Ser
            20                  25                  30 gat ggt ttc agt tat gaa atc tgg tta gat aac acc ggt ggt agc ggt     144
Asp Gly Phe Ser Tyr Glu Ile Trp Leu Asp Asn Thr Gly Gly Ser Gly
        35                  40                  45 tct atg act ctc tgt agt ggt gca acc ttc aag gct gaa tgg aat gca     192
Ser Met Thr Leu Cys Ser Gly Ala Thr Phe Lys Ala Glu Trp Asn Ala
    50                  55                  60
```

```
gct gtt aac cgt ggt aac ttc ctt gcc cgt cgt ggt ctt gac ttc ggt      240
Ala Val Asn Arg Gly Asn Phe Leu Ala Arg Arg Gly Leu Asp Phe Gly
 65              70                  75                  80 tct cga aag aag gca acc gat tac agc tac atc aga ttg gat tat act      288
Ser Arg Lys Lys Ala Thr Asp Tyr Ser Tyr Ile Arg Leu Asp Tyr Thr
                 85                  90                  95 gca act tac aga caa act gcc agt gca agt ggt aac tcc cgt ctc tgt      336
Ala Thr Tyr Arg Gln Thr Ala Ser Ala Ser Gly Asn Ser Arg Leu Cys
            100                 105                 110 gta tac gga tgg ttc caa aac cgt gga gtt caa ggc gtt cct tta gta      384
Val Tyr Gly Trp Phe Gln Asn Arg Gly Val Gln Gly Val Pro Leu Val
        115                 120                 125 gaa tac tac atc att gaa gat tgg gtt gac tgg gtt cca gat gca caa      432
Glu Tyr Tyr Ile Ile Glu Asp Trp Val Asp Trp Val Pro Asp Ala Gln
    130                 135                 140 gga aaa atg gta acc atc gat gga gct caa tat aag att ttc caa atg      480
Gly Lys Met Val Thr Ile Asp Gly Ala Gln Tyr Lys Ile Phe Gln Met
145                 150                 155                 160 gat cac act ggt cca act atc aat ggt ggt agt gaa acc ttt aag caa      528
Asp His Thr Gly Pro Thr Ile Asn Gly Gly Ser Glu Thr Phe Lys Gln
                165                 170                 175 tac ttc agt gtc cgt caa caa aag aga act tct ggt cat att act gtc      576
Tyr Phe Ser Val Arg Gln Gln Lys Arg Thr Ser Gly His Ile Thr Val
            180                 185                 190 tca gat cac ttt aag gaa tgg gct aaa caa ggt tgg ggt att ggt aac      624
Ser Asp His Phe Lys Glu Trp Ala Lys Gln Gly Trp Gly Ile Gly Asn
        195                 200                 205 ctt tat gaa gtt gct ttg aac gcc gaa ggt tgg caa agt agt ggt ata      672
Leu Tyr Glu Val Ala Leu Asn Ala Glu Gly Trp Gln Ser Ser Gly Ile
    210                 215                 220 gct gat gtc acc aag tta gat gtt tac aca acc caa aaa ggt tct aat      720
Ala Asp Val Thr Lys Leu Asp Val Tyr Thr Thr Gln Lys Gly Ser Asn
225                 230                 235                 240 cct acc acc gcc gct cgt act act cgt act act gcc cgt act act gcc      768
Pro Thr Thr Ala Ala Arg Thr Thr Arg Thr Thr Ala Arg Thr Thr Ala
                245                 250                 255 cgt act act acc cgt act agg act ctt cca acc aac aat aag tgt tct      816
Arg Thr Thr Thr Arg Thr Arg Thr Leu Pro Thr Asn Asn Lys Cys Ser
            260                 265                 270 tcc aaa att act gct caa ggt tac gag tgt tgt agt agt cca aat tgt      864
Ser Lys Ile Thr Ala Gln Gly Tyr Glu Cys Cys Ser Ser Pro Asn Cys
        275                 280                 285 gaa att gtc tac act gat gac gat ggt aaa tgg ggt aaa tga              906
Glu Ile Val Tyr Thr Asp Asp Asp Gly Lys Trp Gly Lys
    290                 295                 300

<210> SEQ ID NO 6
<211> LENGTH: 301
<212> TYPE: PRT
<213> ORGANISM: Neocallimastix frontalis

<400> SEQUENCE: 6

Pro Leu Thr Val Ala Lys Ala Gln Trp Gly Arg Gly Ala Ser Ala Gly
 1               5                  10                  15

Gln Lys Leu Ser Val Gly Gly Gln Asn Gln His Lys Gly Val Ser
                 20                  25                  30

Asp Gly Phe Ser Tyr Glu Ile Trp Leu Asp Asn Thr Gly Gly Ser Gly
            35                  40                  45

Ser Met Thr Leu Cys Ser Gly Ala Thr Phe Lys Ala Glu Trp Asn Ala
 50                  55                  60
```

```
Ala Val Asn Arg Gly Asn Phe Leu Ala Arg Arg Gly Leu Asp Phe Gly
 65                  70                  75                  80

Ser Arg Lys Lys Ala Thr Asp Tyr Ser Tyr Ile Arg Leu Asp Tyr Thr
                 85                  90                  95

Ala Thr Tyr Arg Gln Thr Ala Ser Ala Ser Gly Asn Ser Arg Leu Cys
                100                 105                 110

Val Tyr Gly Trp Phe Gln Asn Arg Gly Val Gln Gly Val Pro Leu Val
                115                 120                 125

Glu Tyr Tyr Ile Ile Glu Asp Trp Val Asp Trp Val Pro Asp Ala Gln
            130                 135                 140

Gly Lys Met Val Thr Ile Asp Gly Ala Gln Tyr Lys Ile Phe Gln Met
145                 150                 155                 160

Asp His Thr Gly Pro Thr Ile Asn Gly Gly Ser Glu Thr Phe Lys Gln
                165                 170                 175

Tyr Phe Ser Val Arg Gln Gln Lys Arg Thr Ser Gly His Ile Thr Val
                180                 185                 190

Ser Asp His Phe Lys Glu Trp Ala Lys Gln Gly Trp Gly Ile Gly Asn
            195                 200                 205

Leu Tyr Glu Val Ala Leu Asn Ala Glu Gly Trp Gln Ser Ser Gly Ile
    210                 215                 220

Ala Asp Val Thr Lys Leu Asp Val Tyr Thr Thr Gln Lys Gly Ser Asn
225                 230                 235                 240

Pro Thr Thr Ala Ala Arg Thr Thr Arg Thr Thr Ala Arg Thr Thr Ala
                245                 250                 255

Arg Thr Thr Thr Arg Thr Arg Thr Leu Pro Thr Asn Asn Lys Cys Ser
                260                 265                 270

Ser Lys Ile Thr Ala Gln Gly Tyr Glu Cys Cys Ser Ser Pro Asn Cys
            275                 280                 285

Glu Ile Val Tyr Thr Asp Asp Asp Gly Lys Trp Gly Lys
    290                 295                 300

<210> SEQ ID NO 7
<211> LENGTH: 1233
<212> TYPE: DNA
<213> ORGANISM: Escherichia coli
<220> FEATURE:
<221> NAME/KEY: CDS
<222> LOCATION: (1)..(1233)
<220> FEATURE:
<221> NAME/KEY: misc_feature
<222> LOCATION: (150)..(150)
<223> OTHER INFORMATION: n is a, c, g, or t

<400> SEQUENCE: 7 cag agt gag ccg gag ctg aag ctg gaa agt gtg gtg att gtc agt cgt    48
Gln Ser Glu Pro Glu Leu Lys Leu Glu Ser Val Val Ile Val Ser Arg
 1               5                  10                  15 cat ggt gtg cgt gct cca acc aag gcc acg caa ctg atg cag gat gtc    96
His Gly Val Arg Ala Pro Thr Lys Ala Thr Gln Leu Met Gln Asp Val
                 20                  25                  30 acc cca gac gca tgg cca acc tgg ccg gta aaa ctg ggt tgg ctg aca   144
Thr Pro Asp Ala Trp Pro Thr Trp Pro Val Lys Leu Gly Trp Leu Thr
             35                  40                  45 ccg cgn ggt ggt gag cta atc gcc tat ctc gga cat tac caa cgc cag   192
Pro Arg Gly Gly Glu Leu Ile Ala Tyr Leu Gly His Tyr Gln Arg Gln
         50                  55                  60 cgt ctg gta gcc gac gga ttg ctg gcg aaa aag ggc tgc ccg cag tct   240
Arg Leu Val Ala Asp Gly Leu Leu Ala Lys Lys Gly Cys Pro Gln Ser
```

-continued

```
           65                  70                  75                  80
ggt cag gtc gcg att att gct gat gtc gac gag cgt acc cgt aaa aca         288
Gly Gln Val Ala Ile Ile Ala Asp Val Asp Glu Arg Thr Arg Lys Thr
                     85                  90                  95 ggc gaa gcc ttc gcc gcc ggg ctg gca cct gac tgt gca ata acc gta         336
Gly Glu Ala Phe Ala Ala Gly Leu Ala Pro Asp Cys Ala Ile Thr Val
                    100                 105                 110 cat acc cag gca gat acg tcc agt ccc gat ccg tta ttt aat cct cta         384
His Thr Gln Ala Asp Thr Ser Ser Pro Asp Pro Leu Phe Asn Pro Leu
                115                 120                 125 aaa act ggc gtt tgc caa ctg gat aac gcg aac gtg act gac gcg atc         432
Lys Thr Gly Val Cys Gln Leu Asp Asn Ala Asn Val Thr Asp Ala Ile
            130                 135                 140 ctc agc agg gca gga ggg tca att gct gac ttt acc ggg cat cgg caa         480
Leu Ser Arg Ala Gly Gly Ser Ile Ala Asp Phe Thr Gly His Arg Gln
145                 150                 155                 160 acg gcg ttt cgc gaa ctg gaa cgg gtg ctt aat ttt ccg caa tca aac         528
Thr Ala Phe Arg Glu Leu Glu Arg Val Leu Asn Phe Pro Gln Ser Asn
                    165                 170                 175 ttg tgc ctt aaa cgt gag aaa cag gac gaa agc tgt tca tta acg cag         576
Leu Cys Leu Lys Arg Glu Lys Gln Asp Glu Ser Cys Ser Leu Thr Gln
                180                 185                 190 gca tta cca tcg gaa ctc aag gtg agc gcc gac aat gtc tca tta acc         624
Ala Leu Pro Ser Glu Leu Lys Val Ser Ala Asp Asn Val Ser Leu Thr
            195                 200                 205 ggt gcg gta agc ctc gca tca atg ctg acg gag ata ttt ctc ctg caa         672
Gly Ala Val Ser Leu Ala Ser Met Leu Thr Glu Ile Phe Leu Leu Gln
        210                 215                 220 caa gca cag gga atg ccg gag ccg ggg tgg gga agg atc acc gat tca         720
Gln Ala Gln Gly Met Pro Glu Pro Gly Trp Gly Arg Ile Thr Asp Ser
225                 230                 235                 240 cac cag tgg aac acc ttg cta agt ttg cat aac gcg caa ttt tat ttg         768
His Gln Trp Asn Thr Leu Leu Ser Leu His Asn Ala Gln Phe Tyr Leu
                    245                 250                 255 cta caa cgc acg cca gag gtt gcc cgc agc cgc gcc acc ccg tta tta         816
Leu Gln Arg Thr Pro Glu Val Ala Arg Ser Arg Ala Thr Pro Leu Leu
                260                 265                 270 gat ttg atc aag aca gcg ttg acg ccc cat cca ccg caa aaa cag gcg         864
Asp Leu Ile Lys Thr Ala Leu Thr Pro His Pro Pro Gln Lys Gln Ala
            275                 280                 285 tat ggt gtg aca tta ccc act tca gtg ctg ttt atc gcc gga cac gat         912
Tyr Gly Val Thr Leu Pro Thr Ser Val Leu Phe Ile Ala Gly His Asp
        290                 295                 300 act aat ctg gca aat ctc ggc ggc gca ctg gag ctc aac tgg acg ctt         960
Thr Asn Leu Ala Asn Leu Gly Gly Ala Leu Glu Leu Asn Trp Thr Leu
305                 310                 315                 320 ccc ggt cag ccg gat aac acg ccg cca ggt ggt gaa ctg gtg ttt gaa        1008
Pro Gly Gln Pro Asp Asn Thr Pro Pro Gly Gly Glu Leu Val Phe Glu
                    325                 330                 335 cgc tgg cgt cgg cta agc gat aac agc cag tgg att cag gtt tcg ctg        1056
Arg Trp Arg Arg Leu Ser Asp Asn Ser Gln Trp Ile Gln Val Ser Leu
                340                 345                 350 gtc ttc cag act tta cag cag atg cgt gat aaa acg ccg ctg tca tta        1104
Val Phe Gln Thr Leu Gln Gln Met Arg Asp Lys Thr Pro Leu Ser Leu
            355                 360                 365 aat acg ccg ccc gga gag gtg aaa ctg acc ctg gca gga tgt gaa gag        1152
Asn Thr Pro Pro Gly Glu Val Lys Leu Thr Leu Ala Gly Cys Glu Glu
        370                 375                 380 cga aat gcg cag ggc atg tgt tcg ttg gca ggt ttt acg caa atc gtg        1200
```

```
Arg Asn Ala Gln Gly Met Cys Ser Leu Ala Gly Phe Thr Gln Ile Val
385                 390                 395                 400 aat gaa gca cgc ata ccg gcg tgc agt ttg taa                        1233
Asn Glu Ala Arg Ile Pro Ala Cys Ser Leu
                405                 410

<210> SEQ ID NO 8
<211> LENGTH: 410
<212> TYPE: PRT
<213> ORGANISM: Escherichia coli

<400> SEQUENCE: 8

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
```

```
                340               345               350
Val Phe Gln Thr Leu Gln Gln Met Arg Asp Lys Thr Pro Leu Ser Leu
            355               360               365

Asn Thr Pro Pro Gly Glu Val Lys Leu Thr Leu Ala Gly Cys Glu Glu
        370               375               380

Arg Asn Ala Gln Gly Met Cys Ser Leu Ala Gly Phe Thr Gln Ile Val
385               390               395               400

Asn Glu Ala Arg Ile Pro Ala Cys Ser Leu
            405               410

<210> SEQ ID NO 9
<211> LENGTH: 336
<212> TYPE: DNA
<213> ORGANISM: Ganoderma lucidum
<220> FEATURE:
<221> NAME/KEY: CDS
<222> LOCATION: (1)..(336)

<400> SEQUENCE: 9 atg tcc gac act gcc ttg atc ttc agg ctc gcc tgg gac gtg aag aag      48
Met Ser Asp Thr Ala Leu Ile Phe Arg Leu Ala Trp Asp Val Lys Lys
1               5                  10                  15 ctc tcg ttc gac tac acc ccg aac tgg ggc cgc ggc aac ccc aac aac      96
Leu Ser Phe Asp Tyr Thr Pro Asn Trp Gly Arg Gly Asn Pro Asn Asn
            20                  25                  30 ttc atc gac act gtc acc ttc ccg aaa gtc ttg acc gac aag gcg tac     144
Phe Ile Asp Thr Val Thr Phe Pro Lys Val Leu Thr Asp Lys Ala Tyr
        35                  40                  45 acg tac cgc gtc gcc gtc tcc gga cgg aac ctc ggc gtg aaa ccc tcg     192
Thr Tyr Arg Val Ala Val Ser Gly Arg Asn Leu Gly Val Lys Pro Ser
    50                  55                  60 tac gcg gtc gag agc gac ggc tcg cag aag gtc aac ttc ctc gag tac     240
Tyr Ala Val Glu Ser Asp Gly Ser Gln Lys Val Asn Phe Leu Glu Tyr
65                  70                  75                  80 aac tcc ggg tat ggc ata gcg gac acg aac acg atc cag gtg ttc gtt     288
Asn Ser Gly Tyr Gly Ile Ala Asp Thr Asn Thr Ile Gln Val Phe Val
                85                  90                  95 gtc gac ccc gac acc aac aac gac ttc atc atc gcc cag tgg aac tag     336
Val Asp Pro Asp Thr Asn Asn Asp Phe Ile Ile Ala Gln Trp Asn
            100                 105                 110

<210> SEQ ID NO 10
<211> LENGTH: 111
<212> TYPE: PRT
<213> ORGANISM: Ganoderma lucidum

<400> SEQUENCE: 10

Met Ser Asp Thr Ala Leu Ile Phe Arg Leu Ala Trp Asp Val Lys Lys
1               5                  10                  15

Leu Ser Phe Asp Tyr Thr Pro Asn Trp Gly Arg Gly Asn Pro Asn Asn
            20                  25                  30

Phe Ile Asp Thr Val Thr Phe Pro Lys Val Leu Thr Asp Lys Ala Tyr
        35                  40                  45

Thr Tyr Arg Val Ala Val Ser Gly Arg Asn Leu Gly Val Lys Pro Ser
    50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95
```

Val Asp Pro Asp Thr Asn Asn Asp Phe Ile Ile Ala Gln Trp Asn
            100                 105                 110

<210> SEQ ID NO 11
<211> LENGTH: 720
<212> TYPE: DNA
<213> ORGANISM: Artificial
<220> FEATURE:
<223> OTHER INFORMATION: Synthetic construct of eGFP gene

<400> SEQUENCE: 11

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtga     720
```

<210> SEQ ID NO 12
<211> LENGTH: 708
<212> TYPE: DNA
<213> ORGANISM: Bos taurus
<220> FEATURE:
<221> NAME/KEY: CDS
<222> LOCATION: (1)..(708)

<400> SEQUENCE: 12 att gtc gga gga agt gac tcc aga gaa gga gcc tgg cct tgg gtc gtt        48
Ile Val Gly Gly Ser Asp Ser Arg Glu Gly Ala Trp Pro Trp Val Val
1               5                   10                  15 gct ctg tat ttc gac gat caa cag gtc tgc gga gct tct ctg gtg agc        96
Ala Leu Tyr Phe Asp Asp Gln Gln Val Cys Gly Ala Ser Leu Val Ser
            20                  25                  30 agg gat tgg ctg gtg tcg gcc gcc cac tgc gtg tac ggg aga aat atg       144
Arg Asp Trp Leu Val Ser Ala Ala His Cys Val Tyr Gly Arg Asn Met
        35                  40                  45 gag ccg tct aag tgg aaa gca gtg cta ggc ctg cat atg gca tca aat       192
Glu Pro Ser Lys Trp Lys Ala Val Leu Gly Leu His Met Ala Ser Asn
    50                  55                  60 ctg act tct cct cag ata gaa act agg ttg att gac caa att gtc ata       240
Leu Thr Ser Pro Gln Ile Glu Thr Arg Leu Ile Asp Gln Ile Val Ile
65                  70                  75                  80 aac cca cac tac aat aaa cgg aga aag aac aat gac att gcc atg atg       288
Asn Pro His Tyr Asn Lys Arg Arg Lys Asn Asn Asp Ile Ala Met Met
                85                  90                  95 cat ctt gaa atg aaa gtg aac tac aca gat tat ata cag cct att tgt       336
His Leu Glu Met Lys Val Asn Tyr Thr Asp Tyr Ile Gln Pro Ile Cys
            100                 105                 110 tta cca gaa gaa aat caa gtt ttt ccc cca gga aga att tgt tct att       384
Leu Pro Glu Glu Asn Gln Val Phe Pro Pro Gly Arg Ile Cys Ser Ile
        115                 120                 125

```
gct ggc tgg ggg gca ctt ata tat caa ggt tct act gca gac gta ctg      432
Ala Gly Trp Gly Ala Leu Ile Tyr Gln Gly Ser Thr Ala Asp Val Leu
    130                 135                 140 caa gaa gct gac gtt ccc ctt cta tca aat gag aaa tgt caa caa cag      480
Gln Glu Ala Asp Val Pro Leu Leu Ser Asn Glu Lys Cys Gln Gln Gln
145                 150                 155                 160 atg cca gaa tat aac att acg gaa aat atg gtg tgt gca ggc tat gaa      528
Met Pro Glu Tyr Asn Ile Thr Glu Asn Met Val Cys Ala Gly Tyr Glu
                165                 170                 175 gca gga ggg gta gat tct tgt cag ggg gat tca ggc gga cca ctc atg      576
Ala Gly Gly Val Asp Ser Cys Gln Gly Asp Ser Gly Gly Pro Leu Met
            180                 185                 190 tgc caa gaa aac aac aga tgg ctc ctg gct ggc gtg aca tca ttt gga      624
Cys Gln Glu Asn Asn Arg Trp Leu Leu Ala Gly Val Thr Ser Phe Gly
        195                 200                 205 tat caa tgt gca ctg cct aat cgc cca ggg gtg tat gcc cgg gtg cca      672
Tyr Gln Cys Ala Leu Pro Asn Arg Pro Gly Val Tyr Ala Arg Val Pro
    210                 215                 220 agg ttc aca gag tgg ata caa agt ttt cta cat tag                      708
Arg Phe Thr Glu Trp Ile Gln Ser Phe Leu His
225                 230                 235

<210> SEQ ID NO 13
<211> LENGTH: 235
<212> TYPE: PRT
<213> ORGANISM: Bos taurus

<400> SEQUENCE: 13

Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
            20                  25                  30

Arg Asp Trp Leu Val Ser Ala Ala His Cys Val Tyr Gly Arg Asn Met
        35                  40                  45

Glu Pro Ser Lys Trp Lys Ala Val Leu Gly Leu His Met Ala Ser Asn
    50                  55                  60

Leu Thr Ser Pro Gln Ile Glu Thr Arg Leu Ile Asp Gln Ile Val Ile
65                  70                  75                  80

Asn Pro His Tyr Asn Lys Arg Lys Asn Asn Asp Ile Ala Met Met
                85                  90                  95

His Leu Glu Met Lys Val Asn Tyr Thr Asp Tyr Ile Gln Pro Ile Cys
            100                 105                 110

Leu Pro Glu Glu Asn Gln Val Phe Pro Pro Gly Arg Ile Cys Ser Ile
        115                 120                 125

Ala Gly Trp Gly Ala Leu Ile Tyr Gln Gly Ser Thr Ala Asp Val Leu
    130                 135                 140

Gln Glu Ala Asp Val Pro Leu Leu Ser Asn Glu Lys Cys Gln Gln Gln
145                 150                 155                 160

Met Pro Glu Tyr Asn Ile Thr Glu Asn Met Val Cys Ala Gly Tyr Glu
                165                 170                 175

Ala Gly Gly Val Asp Ser Cys Gln Gly Asp Ser Gly Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
    210                 215                 220
```

Arg Phe Thr Glu Trp Ile Gln Ser Phe Leu His
225                 230                 235

<210> SEQ ID NO 14
<211> LENGTH: 810
<212> TYPE: DNA
<213> ORGANISM: Pseudoalteromonas agarivorans
<220> FEATURE:
<221> NAME/KEY: CDS
<222> LOCATION: (1)..(810)

<400> SEQUENCE: 14

```
gct gat tgg agc tct ttt agt att cca gca caa gca ggc gca ggt aaa       48
Ala Asp Trp Ser Ser Phe Ser Ile Pro Ala Gln Ala Gly Ala Gly Lys
1               5                   10                  15 agc tgg cag tta caa agt gtt tca gat gag ttt aac tac att gca caa       96
Ser Trp Gln Leu Gln Ser Val Ser Asp Glu Phe Asn Tyr Ile Ala Gln
                20                  25                  30 cct aat aat aaa cca gct gct ttt aat aat cgt tgg aac gca tct tat      144
Pro Asn Asn Lys Pro Ala Ala Phe Asn Asn Arg Trp Asn Ala Ser Tyr
            35                  40                  45 ata aat gct tgg cta ggt cct ggc gat aca gaa ttt agc gct ggc cac      192
Ile Asn Ala Trp Leu Gly Pro Gly Asp Thr Glu Phe Ser Ala Gly His
        50                  55                  60 tca tat aca act ggc ggg gcg ctt ggt ctg caa gca acc gaa aaa gca      240
Ser Tyr Thr Thr Gly Gly Ala Leu Gly Leu Gln Ala Thr Glu Lys Ala
65                  70                  75                  80 ggt acg aac aaa gtt ctc tca ggt att att tct tct aaa gca acc ttt      288
Gly Thr Asn Lys Val Leu Ser Gly Ile Ile Ser Ser Lys Ala Thr Phe
                85                  90                  95 act tac ccc cta tac cta gag gcg atg gta aaa cca aca aac aac act      336
Thr Tyr Pro Leu Tyr Leu Glu Ala Met Val Lys Pro Thr Asn Asn Thr
                100                 105                 110 atg gca aat gct gta tgg atg ctt agt gct gat tct acc caa gaa atc      384
Met Ala Asn Ala Val Trp Met Leu Ser Ala Asp Ser Thr Gln Glu Ile
            115                 120                 125 gat gct atg gag tca tat ggt agc gac cga att ggc caa gag tgg ttt      432
Asp Ala Met Glu Ser Tyr Gly Ser Asp Arg Ile Gly Gln Glu Trp Phe
        130                 135                 140 gac caa cgt atg cat gtt agt cat cac ata ttt att cga gac cca ttt      480
Asp Gln Arg Met His Val Ser His His Ile Phe Ile Arg Asp Pro Phe
145                 150                 155                 160 caa gat tac cag cca aag gac gct ggc tct tgg gtt tac aac aac gga      528
Gln Asp Tyr Gln Pro Lys Asp Ala Gly Ser Trp Val Tyr Asn Asn Gly
                165                 170                 175 gaa aca tac cgc aat aaa ttt cgt aga tat gga gta cat tgg aag gat      576
Glu Thr Tyr Arg Asn Lys Phe Arg Arg Tyr Gly Val His Trp Lys Asp
                180                 185                 190 gcg tgg aat tta gat tac tat ata gat ggt gtt ttg gtt cga agt gtc      624
Ala Trp Asn Leu Asp Tyr Tyr Ile Asp Gly Val Leu Val Arg Ser Val
            195                 200                 205 tct ggc cca aat att att gat cct gaa aac tat act aac gga aca ggc      672
Ser Gly Pro Asn Ile Ile Asp Pro Glu Asn Tyr Thr Asn Gly Thr Gly
        210                 215                 220 tta aac aag cct atg cac ata ata ctg gat atg gaa cat cag cca tgg      720
Leu Asn Lys Pro Met His Ile Ile Leu Asp Met Glu His Gln Pro Trp
225                 230                 235                 240 cga gac gtt aag cct aat gca tct gag ctt gca gat ccc aat aaa agt      768
Arg Asp Val Lys Pro Asn Ala Ser Glu Leu Ala Asp Pro Asn Lys Ser
                245                 250                 255 ata ttt tgg gta gat tgg ata cga gtt tat aaa gcc cag taa             810
Ile Phe Trp Val Asp Trp Ile Arg Val Tyr Lys Ala Gln
```

```
Ile Phe Trp Val Asp Trp Ile Arg Val Tyr Lys Ala Gln
            260                 265

<210> SEQ ID NO 15
<211> LENGTH: 269
<212> TYPE: PRT
<213> ORGANISM: Pseudoalteromonas agarivorans

<400> SEQUENCE: 15

Ala Asp Trp Ser Ser Phe Ser Ile Pro Ala Gln Ala Gly Ala Gly Lys
1               5                   10                  15

Ser Trp Gln Leu Gln Ser Val Ser Asp Glu Phe Asn Tyr Ile Ala Gln
            20                  25                  30

Pro Asn Asn Lys Pro Ala Ala Phe Asn Asn Arg Trp Asn Ala Ser Tyr
            35                  40                  45

Ile Asn Ala Trp Leu Gly Pro Gly Asp Thr Glu Phe Ser Ala Gly His
50                  55                  60

Ser Tyr Thr Thr Gly Gly Ala Leu Gly Leu Gln Ala Thr Glu Lys Ala
65                  70                  75                  80

Gly Thr Asn Lys Val Leu Ser Gly Ile Ile Ser Ser Lys Ala Thr Phe
                85                  90                  95

Thr Tyr Pro Leu Tyr Leu Glu Ala Met Val Lys Pro Thr Asn Asn Thr
            100                 105                 110

Met Ala Asn Ala Val Trp Met Leu Ser Ala Asp Ser Thr Gln Glu Ile
            115                 120                 125

Asp Ala Met Glu Ser Tyr Gly Ser Asp Arg Ile Gly Gln Glu Trp Phe
            130                 135                 140

Asp Gln Arg Met His Val Ser His His Ile Phe Ile Arg Asp Pro Phe
145                 150                 155                 160

Gln Asp Tyr Gln Pro Lys Asp Ala Gly Ser Trp Val Tyr Asn Asn Gly
                165                 170                 175

Glu Thr Tyr Arg Asn Lys Phe Arg Arg Tyr Gly Val His Trp Lys Asp
            180                 185                 190

Ala Trp Asn Leu Asp Tyr Tyr Ile Asp Gly Val Leu Val Arg Ser Val
            195                 200                 205

Ser Gly Pro Asn Ile Ile Asp Pro Glu Asn Tyr Thr Asn Gly Thr Gly
            210                 215                 220

Leu Asn Lys Pro Met His Ile Ile Leu Asp Met Glu His Gln Pro Trp
225                 230                 235                 240

Arg Asp Val Lys Pro Asn Ala Ser Glu Leu Ala Asp Pro Asn Lys Ser
                245                 250                 255

Ile Phe Trp Val Asp Trp Ile Arg Val Tyr Lys Ala Gln
            260                 265
```

METHOD FOR INCREASING THERMAL STABILITY AND RETAINING ACTIVITY OF A PROTEIN

CROSS REFERENCE TO RELATED APPLICATIONS

This application is a Continue-in-part Application of U.S. patent application Ser. No. 12/777,308, filed May 11, 2010, which claims priority to the following: U.S. Provisional Patent Application No. 61/178,816 filed on May 15, 2009, U.S. The disclosures of said applications are hereby expressly incorporated by reference in its entirety.

FIELD OF THE INVENTION

The present invention relates to a method and a system for increasing stability and retaining activity of a protein, and more particularly relates to the method and the system using starch binding protein.

BACKGROUND OF THE INVENTION

Production of proteins by expression in microbial systems has become a significant source of high value, medically important proteins. Purification and recovery of recombinant proteins are major considerations in the design of a fermentation process. While traditional methods of protein purification can be used to isolate a product, improved methods include the use of recombinant proteins. Recombinant proteins can be purified by affinity column chromatography, the desired component of the recombinant protein being purified by virtue of its covalent attachment to a polypeptide, which binds to an affinity matrix.

Certain systems exist for isolating proteins by the principle of affinity column chromatography.

U.S. Pat. No. 5,643,758 describes a system comprising maltose-binding protein (MBP). A cloned gene is inserted into a pMAL vector down-stream from the malE gene, which encodes MBP. The vector is transformed to a host cell, then the recombinant protein can express in the host cell. The cell lysate or media fraction is loaded to a column containing affinity matrix amylose and washed several times, then using a large amount of maltose to elute the recombinant protein.

U.S. Pat. No. 5,202,247 describes a system comprising cellulose-binding domain. A cellulose column can be used to purify the recombinant protein that contains cellulose-binding domain. The cell lysate or media fraction is loaded to the column and washed. The interaction between cellulose-binding domain and cellulose appears to be driven by hydrophobic interaction at neutral pH. The general method for elution used low polarity solvents such as ethylene glycol, prior to removal of the low polarity solvents by dialysis and filtration.

These current protein purification systems have some disadvantages. The purification processes are inconvenient and laborious. The columns used in purification are expensive. Limitations for protein purification of these systems include unable to isolate the recombinant protein in certain conditions such as EDTA-containing samples as well as the current protein tags being used are relatively large as compared to the target protein bigger than that of this invention.

There are some problems utilizing enzyme products for aquatic feed at present, such as (a) enzyme quickly flows away after feed is added into water, and (b) enzyme activity will be destructed when feed pelleting temperature is higher than 100° C.

SUMMARY OF THE INVENTION

Figure 1:
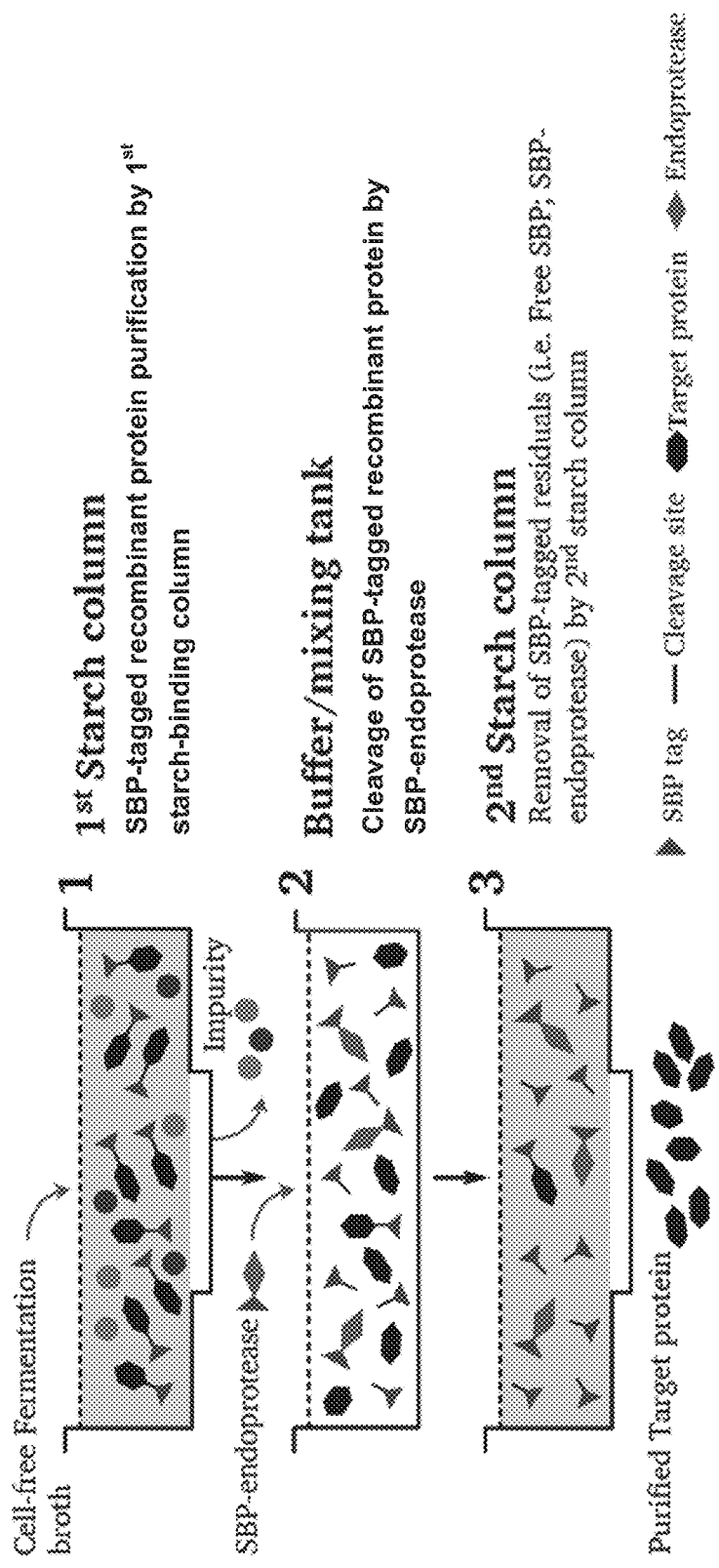
FIG. 1 shows a system designed for highly specific cleavage of fusion proteins followed by the rapid, affinity-based capture and removal of all SBP-tagged residuals (i.e. SBP-tagged endoprotease; SBP-tagged target protein; free SBP).

The present invention provides a method for increasing thermal stability of a target protein, comprising: (a) fusing a starch binding protein (SBP) with the target protein to form a SBP-tagged recombinant protein; (b) expressing the SBP-tagged recombinant protein by an eukaryotic expression host; and (c) combining the SBP-tagged recombinant protein with a SBP-binding matrix.

The present invention also provides a method for retaining an activity of a target protein in aquatic environment, comprising: (a) fusing a starch binding protein (SBP) with the target protein to form a SBP-tagged recombinant protein; (b) expressing the SBP-tagged recombinant protein by an expression host; and (c) combining the SBP-tagged recombinant protein with a SBP-binding matrix.

DETAILED DESCRIPTION OF THE INVENTION

In describing and claiming the invention, the following terminology will be used in accordance with the definitions set forth below.

As used herein, the term "recombinant protein" is a protein that is derived from recombinant DNA. The term "recombinant DNA" is a form of DNA that does not exist naturally, which is created by combining DNA sequences that would not normally occur together.

The term "starch binding protein" as used herein will be abbreviated as "SBP" and is meant to define all polypeptide having affinity for binding to starch.

The term "SBP tag(s)" used herein is affinity tags of SBP and the term "affinity tags" is tags appended to proteins so that they can be purified from their crude biological source using an affinity technique.

The term "SBP-tagged recombinant protein" as used herein refers to a recombinant protein which has peptide sequences of SBP genetically grafted onto as affinity tags.

The term "SBP-binding matrix" herein refers to any types of matrix that is capable of binding with SBP. Examples of SBP-binding matrix include, but are not limited to, starch, amylopectin, amylose resin, dextrin resin and alginate beads.

As used herein, the term "SBP-endoprotease" refers to any types of endoprotease that is capable of binding with SBP as tags. Endoprotease is an enzyme that cleaves the peptide bonds of nonterminal amino acids (i.e. within the molecule). Examples of SBP-endoprotease include, but are not limited to, SBP-SARS protease or SBP-enterokinase. The practices of this invention are hereinafter described in detail with respect to a method and system for purifying a target protein by use of a re-usable, convenient and low cost SBP-tagged recombinant protein and SBP-binding matrix.

In some embodiments, a method is provided for purifying a recombinant protein, comprising
  (a) providing a solution including a starch binding protein (SEQ ID NO: 2) (SBP)-tagged recombinant protein;
  (b) adding the solution into a first container containing a SBP-binding matrix;
  (c) eluting an alkaline buffer into the first container of step (b) to obtain a mixture;
  (d) mixing the mixture with a solution for cleavage of a SBP and a recombinant protein in a second container to produce a reaction mixture; and
  (e) adding the reaction mixture into a third container containing SBP-binding matrix to recover the recombinant protein.

In some embodiments of the present invention, wherein the SBP-binding matrix includes starch, amylopectin, amylose resin, dextrin resin or alginate beads.

In some embodiments, the present invention provides a method for purifying a recombinant protein comprising the steps of
  (a) providing a solution including a starch binding protein (SBP)-tagged recombinant protein from a cell;
  (b) adding the solution into a first container containing starch matrix;
  (c) eluting an alkaline buffer into the first container of step (b) to
  (d) mixing the mixture with a solution for cleavage of a SBP and a recombinant protein in a second container to produce a reaction mixture; and
  (e) adding the reaction mixture into a third container containing starch matrix to recover the recombinant protein.

In the preferred embodiment, the first container in step (b), the second container in step (d) or the third container in step (e) is in a disposable form. The mixture in step (d) is further added by SBP-endoprotease. In the most preferred embodiment, the SBP-endoprotease is SBP-SARS protease or SBP-enterokinase.

In the preferred embodiment, the solution in step (a) has a pH of 4 to 6, and the buffer in step (c) has a pH of 7 to 11. In the most preferred embodiment, the solution in step (a) has a pH of 5 to 6, and the buffer in step (c) has a pH of 8 to 9. Although the buffer in step (c) has the best discharge effect when pH is 11, excessive alkaline condition may destroy the target proteins. Therefore, recommend pH range of the buffer is from 8 to 9. The buffer can also discharge the protein when pH is of 2 to 4, but the alkaline condition is recommended.

In the preferred embodiment, the starch binding protein (SBP)-tagged recombinant protein has endoprotease recognition site between SBP and target protein. In some embodiment, the solution in step (b) has a pH of 4 to 8 to recover the SBP-tagged recombinant protein. In some preferred embodiment, the pH is 5 to 7 is recommended.

In some embodiments, the method further comprises a neutralizing step before the step (e) for adjusting a pH until 5 to 7. Additionally, the reaction mixture of the third container recover the tag-free recombinant protein while the SBP tag, SBP-endoprotease and undigested SBP-tagged recombinant were captured on SBP-binding matrix.

The present invention also provides a system for purifying a recombinant protein comprising
  (a) a means for providing a solution including a SBP-tagged recombinant protein from a cell;
  (b) a means for adding the solution into a first container containing SBP-binding matrix;
  (c) a means for eluting an alkaline buffer into the first container of (b) to obtain a mixture;
  (d) a means for mixing the mixture with a solution for cleavage of a SBP and a recombinant protein in a second container to produce a reaction mixture; and
  (e) a means for adding the reaction mixture into a third container containing SBP-binding matrix to recover the recombinant protein.

In some embodiments of the present invention, wherein the SBP-binding matrix includes starch, amylopectin, amylose resin, dextrin resin or alginate beads.

In the preferred embodiment, the first container of (b), the second container of (d) or the third container of (e) is in a disposable form. The mixture of (d) is further added by SBP-endoprotease. In the most preferred embodiment, the SBP-endoprotease is SBP-SARS protease or SBP-enterokinase.

In the preferred embodiment, the solution of (a) has a pH of 4 to 6, and the buffer of (c) has a pH of 7 to 11. In the most preferred embodiment, the solution of (a) has a pH of 5 to 6, and the buffer of (c) has a pH of 8 to 9.

In the preferred embodiment, the starch binding protein (SBP)-tagged recombinant protein has endoprotease recognition site between SBP and target protein. In some embodiments, the solution of (b) has a pH of 4 to 8 to recover the SBP-tagged recombinant protein. In some preferred embodiments, the pH is 5 to 7 is recommended.

In some embodiments, the system further comprises a neutralizing means before the means of (e) for adjusting a pH until 5 to 7. Additionally, the reaction mixture of the third container recover the tag-free recombinant protein while the SBP tag, SBP-endoprotease and undigested SBP-tagged recombinant were captured on SBP-binding matrix.

In some embodiments, a recombinant protein with thermal stability is provided which is prepared by the method of the any of the above-described embodiments, wherein the recombinant protein is fused by a SBP tag and a target protein. In particular embodiments, the target protein is Lipase, Xylanase or Phytase. Thus, the thermal stability of proteins can increase easily and the expand application fields very extensively.

In other embodiments, a method is provided for preparing a recombinant protein comprising a SBP tag and a protein A, wherein the recombinant protein is expressed by yeast or bacteria. In particular embodiments, the yeast is *Pichia pastoris*. In particular embodiments, the bacteria are *E. coli*. The disclosure therefore is useful in any application where purification of a protein is desirable, such as diagnostics, research uses and industrial applications.

The present invention also provides a method for increasing thermal stability of a target protein, comprising:
  (a) fusing a starch binding protein (SBP) (such as SEQ ID NO: 2) with the target protein to form a SBP-tagged recombinant protein;
  (b) expressing the SBP-tagged recombinant protein by an eukaryotic expression host; and
  (c) combining the SBP-tagged recombinant protein with a SBP-binding matrix.

In some embodiments, the eukaryotic expression host is selected from a yeast, an insect cell or a mammalian cell.

Additionally, the yeast is selected from *Pichia pastoris*, *Pichia methanolica*, *Saccharomyces cerevisiae*, *Yarrowia lipolytica* or *Kluyveromyces lactis*.

In some embodiments, the target protein is an enzyme and in the preferred embodiments, the enzyme is selected from phytase (SEQ ID NO: 8), lipase (SEQ ID NO: 4), xylanase (SEQ ID NO: 6), protease, agarase (SEQ ID NO: 15), cellulase, oxidase or dehydrogenase. In the more preferred embodiments, the protease is selected from endoprotease, SARS protease or enterokinase (SEQ ID NO: 13).

In other embodiments, the target protein is selected from immunoregulatory protein, fluorescence protein or protein A. In the more preferred embodiments, the immunoregulatory protein is LZ8 (SEQ ID NO: 10); the fluorescence protein is eGFP and the protein A is lectin.

Still in other embodiments, the combination of the SBP-tagged protein with the SBP-binding matrix is used as an animal feed, a dietary supplement, a medical formulation or an immobilized catalyst. Additionally, the SBP-binding matrix is selected from starch, alginate, amylopectin, dextrin resin or amylose resin.

The present invention also provides a method for retaining an activity of a target protein in aquatic environment, comprising:
(a) fusing a starch binding protein (SBP) (such as SEQ ID NO: 2) with the target protein to form a SBP-tagged recombinant protein;
(b) expressing the SBP-tagged recombinant protein by an expression host; and
(c) combining the SBP-tagged recombinant protein with a SBP-binding matrix.

In some embodiments, the expression host is a bacterium, a yeast, an insect cell or a mammalian cell. Additionally, the yeast is selected from *Pichia pastoris* or *Saccharomyces cerevisiae* and the bacterium is selected from *E. coli*, *Bacillus subtilis* or *Brevibacillus choshinensis*.

In some embodiments, the target protein is an enzyme and in the preferred embodiments, the enzyme is selected from phytase (SEQ ID NO: 8), lipase (SEQ ID NO: 4), xylanase (SEQ ID NO: 6), protease, agarase (SEQ ID NO: 15), cellulase, oxidase or dehydrogenase. In the more preferred embodiments, the protease is selected from endoprotease, SARS protease or enterokinase (SEQ ID NO: 13).

In other embodiments, the target protein is selected from immunoregulatory protein, fluorescence protein or protein A. In the more preferred embodiments, the immunoregulatory protein is LZ8 (SEQ ID NO: 10); the fluorescence protein is eGFP and the protein A is lectin.

Still in other embodiments, the combination of the SBP-tagged protein with the SBP-binding matrix is used as an animal feed, a dietary supplement, a medical formulation or an immobilized catalyst. Additionally, the SBP-binding matrix is selected from starch, alginate, amylopectin, dextrin resin or amylose resin.

EXAMPLE

The following example was offered by the way of illustration and not by the way of limitation.

Example 1

Protein Purification

Construction and Expression of SBP-Tagged Protein

The SBP (starch binding protein) gene (SEQ ID NO: 1) was PCR amplified and fused to the N-terminal of target protein with an endoprotease cleavage site between the SBP and target protein gene. The fusion protein gene was then cloned into *Pichia pastoris* expression vector pPICZαA under control of AOX1 promoter and transformed into *Pichia pastoris* GS115 for expression. The *Pichia pastoris* transformant harboring SBP-target protein gene was cultivated in BMGY media for 24 hours. The cells were recovered by centrifugation and resuspended in BMMY containing 0.5% methanol. Methanol (0.5% v/v) was added every 24 hour in order to induce the expression of SBP-tagged recombinant protein. After induction for 5 days, the cells were removed by centrifugation and the cell-free fermentation broth was collected for downstream purification.

The agarase gene (SEQ ID NO: 14) was PCR amplified from the chromosomal DNA of *Pseudoalteromonas agarivoran* BCRC17819 and fused to the C-terminal of SBP with an endoprotease cleavage site between the SBP and target protein gene. The fusion protein gene was then cloned into the *Brevibacillus choshinensis* expression vector pNCMO2 (Takara) and transformed into *Brevibacillus choshinensis* SP3 for expression according to the product manual. The *Brevibacillus choshinensis* transformant harboring SBP-agarase gene was cultivated in TM media (1% glucose, 1% polypeptone, 0.5% meat extract, 0.2% yeast extract, 10 mg/L $FeSO_4 \cdot 7H_2O$, 10 mg/L $MnSO_4 \cdot 4H_2O$, 1 mg/L $ZnSO_4 \cdot 7H_2O$, pH 7.0) at 30° C. for 48 hours. The cells were removed by centrifugation and the cell-free fermentation broth was collected for downstream purification.

Purification of SBP-Tagged Recombinant Protein by $1^{st}$ Starch Column

The cell-free fermentation broth was applied to the $1^{st}$ starch column (FIG. 1). The SBP-tagged recombinant protein was bound on starch and the impurity flew through. The bounded SBP-tagged recombinant protein can be eluted by glycine buffer pH 11 followed by the dialysis against Tris buffer pH 7.4 for storage.

Endoprotease Cleavage of SBP-Tagged Recombinant Protein

The eluted SBP-tagged recombinant protein was mixed with SBP-endoprotease in appropriate buffer. The protease recognition site between SBP-tag and target protein may be cleaved by SBP-protease for SBP-tag removal.

Purification of Tag-Free Target Protein

After SBP-endoprotease treatment, the reaction mixture was applied to the $2^{nd}$ starch column. The impurities comprising free SBP, SBP-endoprotease and uncut SBP-tagged recombinant protein may be captured by starch column. The completely digested target protein with native N-termini was recovered in the flow through fraction.

Example 2

Comparison of Thermostability

The SBP gene (SEQ ID NO: 1) was PCR amplified and fused to the N-termini of target enzyme. The Lipase gene (SEQ ID NO: 3) from *R. oryzae*, Xylanase gene (SEQ ID NO: 5) from the unpurified ruminal fungal culture and the Phytase gene (SEQ ID NO: 7) from *E. coli* were cloned and fused to the SBP. The SBP-Lipase, SBP-Xylanase and SBP-Phytase fusion proteins were expressed by the method described above and used in the present invention.

Thermal Stability of Lipase from Different Sources

One unit of Lipase activity (U) was defined when the sample released 1 μmole p-Nitrophenol per minute in 0.3 mM 4-Nitrophenyl palmitate under 30° C., pH 7.0. SBP-Lipase (52500 U/g) and F-AP15 Lipase (32430 U/g, *R. oryzae* Lipase purchased from Amano Enzyme Inc.) were mixed with fermented soybean meal of water content of 15% or 20% to reach 1000 per gram. The mixed 100 U/g Lipase from different sources was weighted to pick 12 g into 100 ml serum vial. The serum vial with sample therein was locked and autoclaved with 85° C. or 90° C. for ten minutes. Each condition of each Lipase was tested double times. After treatment, the activity of Lipase was measured. The results were shown in Table 1 and Table 2.

TABLE 1

Fermented soybean meal with 15% total water content

| Sample name | Treating temp. (° C.) | Treating time (min) | Percentage (%) |
| --- | --- | --- | --- |
| SBP-Lipase | 25° C. | 0 | 100% |
| SBP-Lipase | 85° C. | 10 | 86.78% |
| SBP-Lipase | 90° C. | 10 | 86.2% |
| F-AP15 | 25° C. | 0 | 100% |
| F-AP15 | 85° C. | 10 | 66.82% |
| F-AP15 | 90° C. | 10 | 37.02% |

TABLE 2

Fermented soybean meal with 20% total water content

| Sample name | Treating temp. (° C.) | Treating time (min) | Percentage (%) |
| --- | --- | --- | --- |
| SBP-Lipase | 25° C. | 0 | 100% |
| SBP-Lipase | 85° C. | 10 | 75% |
| SBP-Lipase | 90° C. | 10 | 58% |
| F-AP15 | 25° C. | 0 | 100% |
| F-AP15 | 85° C. | 10 | 19.61% |
| F-AP15 | 90° C. | 10 | 8.56% |

The data showed that the thermal stability of SBP-Lipase was obviously better than F-AP15 Lipase. Under the condition of fermented soybean meal with 15% water content, the residual activity of SBP-Lipase was 86.78% and the residual activity of F-AP15 Lipase was 66.82% after heating 85° C. for 10 minutes. After heating 90° C. for 10 minutes, the residual activity of SBP-Lipase was still 86.2% but the residual activity of F-AP15 Lipase was just 37.02%.

Under the condition of fermented soybean meal with 20% water content, the residual activity of SBP-Lipase was 75% and the residual activity of F-AP15 Lipase was 19.61% after heating 85° C. for 10 minutes. After heating 90° C. for 10 minutes, the residual activity of SBP-Lipase was still 58% but the residual activity of F-AP15 Lipase was just 8.56%.

Thermal Stability of Xylanase from Different Sources

One unit of Xylanase activity (U) was defined when the sample released 1 μmole xylose per minute in 1.2% (w/v) xylan under 50° C., pH 5.3. SBP-Xylanase (3028 U/g) and Xylanase (304 U/g, Xylanase without SBP expressed in *P. pastoris*) were mixed with fermented soybean meal of water content of 15% or 20% to reach 100 U/g. The mixed 100 U/g Xylanase from different sources was weighted to pick 12 g into 100 ml serum vial. The serum vial with sample therein was locked and autoclaved with 85° C. or 90° C. for ten minutes. After treatment, the activity of Xylanase was measured. The results were shown in Table 3 and Table 4.

TABLE 3

Fermented soybean meal with 15% total water content

| Sample name | Treating temp. (° C.) | Treating time (min) | Percentage (%) |
| --- | --- | --- | --- |
| SBP-Xylanase | 25° C. | 0 | 100% |
| SBP-Xylanase | 85° C. | 10 | 96.40% |
| SBP-Xylanase | 90° C. | 10 | 91.01% |
| Xylanase | 25° C. | 0 | 100% |
| Xylanase | 85° C. | 10 | 85.43% |
| Xylanase | 90° C. | 10 | 79.52% |

TABLE 4

Fermented soybean meal with 20% total water content

| Sample name | Treating temp. (° C.) | Treating time (min) | Percentage (%) |
| --- | --- | --- | --- |
| SBP-Xylanase | 25° C. | 0 | 100% |
| SBP-Xylanase | 85° C. | 10 | 93.79% |
| SBP-Xylanase | 90° C. | 10 | 86.27% |
| Xylanase | 25° C. | 0 | 100% |
| Xylanase | 85° C. | 10 | 84% |
| Xylanase | 90° C. | 10 | 79% |

The data showed that the thermal stability of SBP-Xylanase was better than Xylanase without SBP-tag. Under the condition of fermented soybean meal with 15% water content, the residual activity of SBP-Xylanase was 96.40% and the residual activity of Xylanase was 85.43% after heating 85° C. for 10 minutes. After heating 90° C. for 10 minutes, the residual activity of SBP-Xylanase was 91.01% and the residual activity of Xylanase was 79.52%.

Under the condition of fermented soybean meal with 20% water content, the residual activity of SBP-Xylanase was 93.79% and the residual activity of Xylanase was 84% after heating 85° C. for 10 minutes. After heating 90° C. for 10 minutes, the residual activity of SBP-Xylanase was 86.27% but the residual activity of Xylanase was 79%.

Thermal Stability of Phytase from Different Sources

One unit of Phytase activity (U) is defined as the amount of enzyme needed for the release of 1 μmol inorganic phosphorus (P) from 1.5 mM-sodium phytate per minute at pH 5.0 and 37° C. SBP-Phytase (10500 U/g) and Phytase without SBP (6972 U/g) were mixed with fermented soybean meal of water content of 15% or 20% to reach 1000 per gram. The mixed 100 U/g Phytase from different sources was weighted to pick 12 g into 100 ml serum vial. The serum vial with sample therein was locked and autoclaved with 85° C. or 90° C. for ten minutes. Each condition of each Phytase was tested double times. After treatment, the activity of Phytase was measured. The results were shown in Table 5 and Table 6.

TABLE 5

Fermented soybean meal with 15% total water content

| Sample name | Treating temp. (° C.) | Treating time (min) | Percentage (%) |
| --- | --- | --- | --- |
| SBP-Phytase | 25° C. | 0 | 100% |
| SBP-Phytase | 85° C. | 10 | 88.1% |
| SBP-Phytase | 90° C. | 10 | 74.3% |
| Phytase | 25° C. | 0 | 100% |
| Phytase | 85° C. | 10 | 82.8% |
| Phytase | 90° C. | 10 | 59.5% |

TABLE 6

Fermented soybean meal with 20% total water content

| Sample name | Treating temp. (° C.) | Treating time (min) | Percentage (%) |
|---|---|---|---|
| SBP-Phytase | 25° C. | 0 | 100% |
| SBP-Phytase | 85° C. | 10 | 76.6% |
| SBP-Phytase | 90° C. | 10 | 48.5% |
| Phytase | 25° C. | 0 | 100% |
| Phytase | 85° C. | 10 | 55% |
| Phytase | 90° C. | 10 | 28.9% |

Development of Aquatic Feed Product

Figure 2:
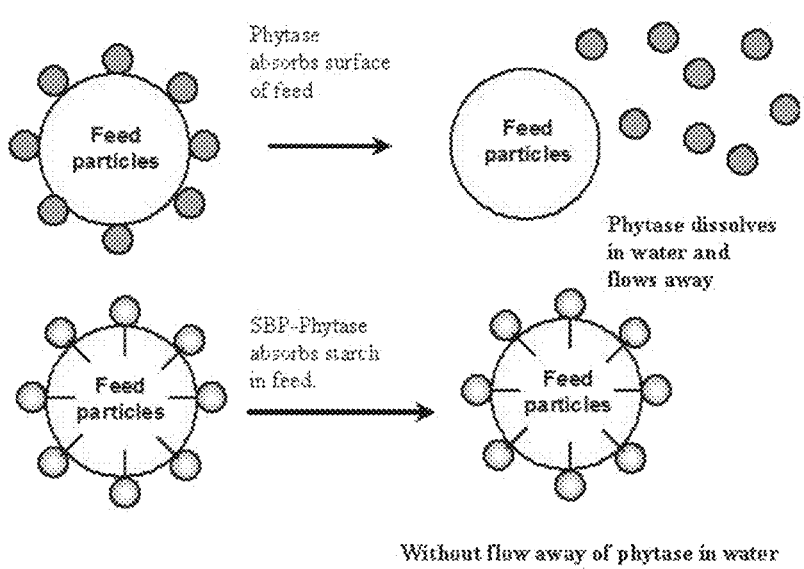
FIG. 2 shows a diagram of SBP-Phytase and Phytase in the water.
Figure 3A:
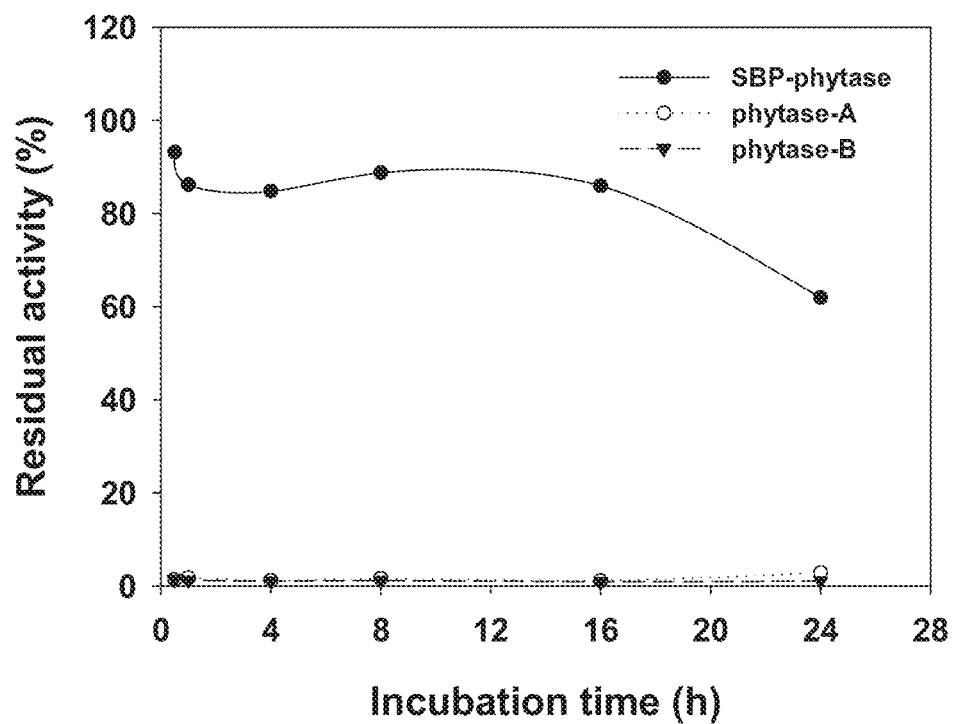
FIG. 3 shows the result of a releasing experiment of SBP-tagged proteins in water. (A) shows the result of SBP-Phytase. (B) shows the result of SBP-Agarase.

The present invention demonstrated that SBP-Phytase was adapted to being utilized for aquatic feed by (a) absorbing starch to immobilize enzyme on aquatic feed so that the enzyme would not flow away easily when the feed was added into water, and (b) increasing thermostability substantially of the enzyme. FIG. 2 shows a diagram of SBP-Phytase and Phytase in the water. FIG. 3(A) shows the result of a releasing experiment of SBP-Phytase in water. 0.4 g Phytase powder from different sources was added into 40 ml pure water, and vortexed at 25° C. The solution was then centrifuged at 3000 rpm for 30 minutes. 5 ml acetate buffer (pH 6.0) was added to the precipitate and vibrated by an ultrasonic vibrator for 30 minutes. Finally, the activity of Phytase was determined. Phytase of A or B company flowed away in water quickly after they were added into the water. Contrarily, SBP-Phytase still maintained at least 80% activity after being added into water in 16 hours.

Figure 3B:
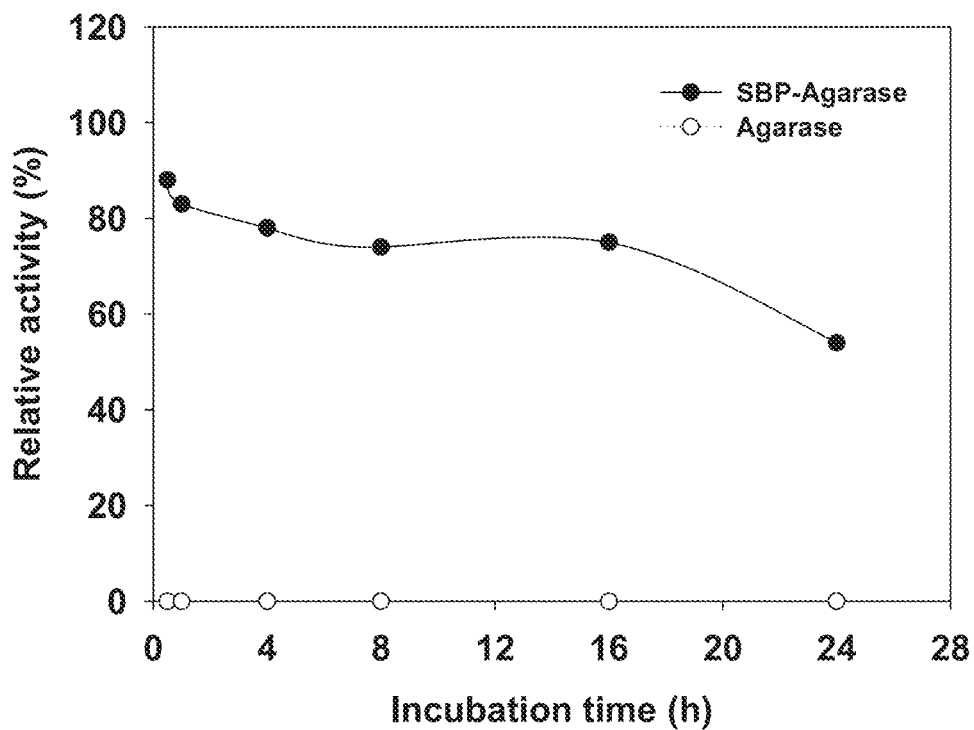

FIG. 3(B) shows the result of a releasing experiment of SBP-Agarase in water. One unit of agarase activity (U) was defined when the sample released 1 μmole galactose per minute in 0.2% (w/v) agaose (dissolved in 50 mM imidazole/HCl, pH 6.5) under 37° C. SBP-Agarase and Agarase (Agarase without SBP expressed in *Brevibacillus choshinensis*) (SEQ ID NO: 15) were mixed with starch reach 10 U/g. 1.0 g of SBP-Agarase or Agarase powder was added into 10 ml pure water and vortexed at 25° C. The solution was then centrifuged at 3000 rpm for 30 minutes. 5 ml acetate buffer (pH 6.0) was added to the precipitate and vibrated by an ultrasonic vibrator for 30 minutes. Finally, the activity of Agarase was determined. Agarase without SBP flowed away in water quickly after they were added into the water. Contrarily, SBP-Agarase still maintained at least 70% activity after being added into water in 16 hours.

Example 3

Binding Assay of SBD-eGFP to Different Types of SBP Matrixes

Binding Assay of SBD-eGFP to Different Types of Resin

Figure 4A:
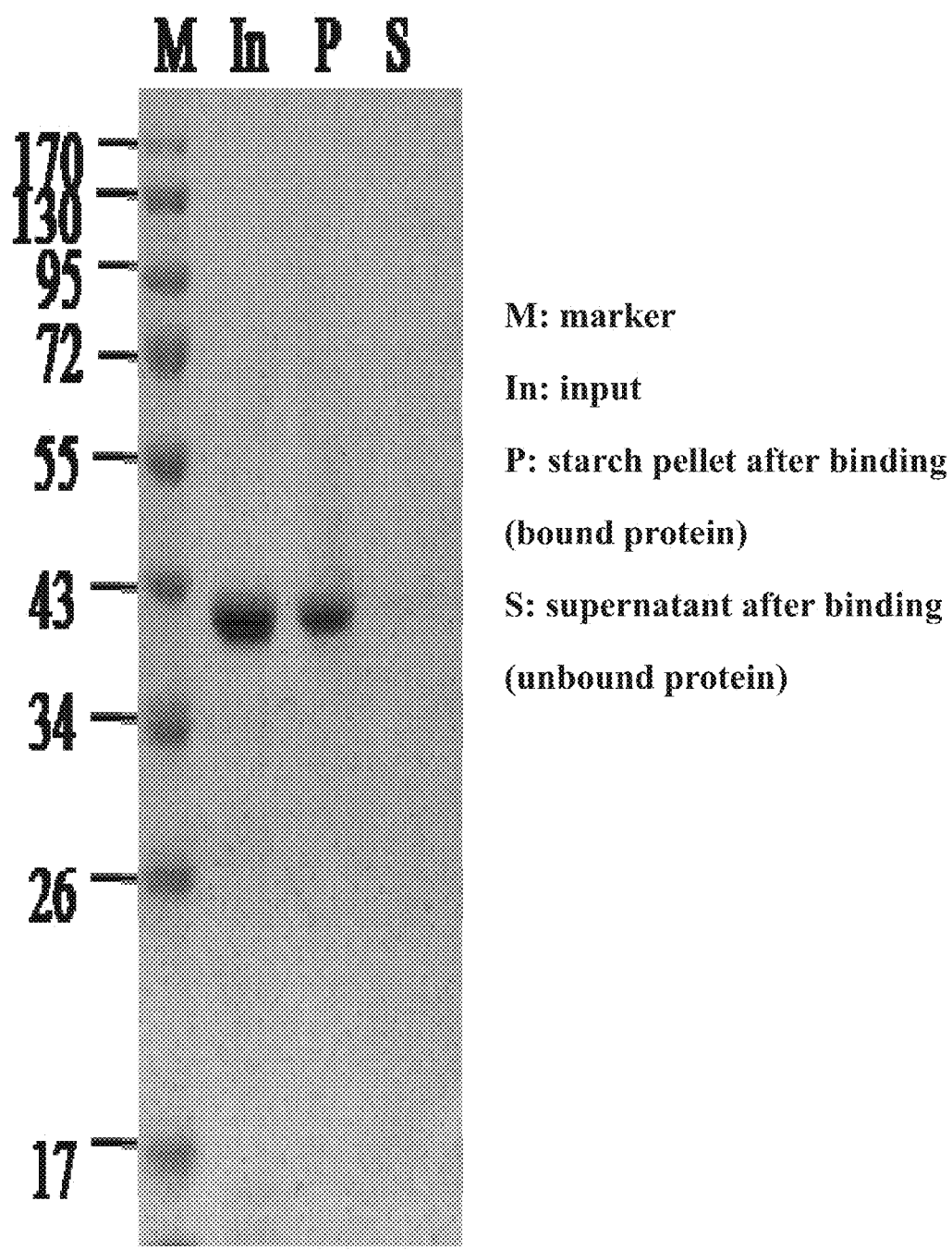
FIG. 4 shows the SDS-PAGE result of binding assay of SBD-eGFP to different types of resin. (A) shows the result of amylopectin. (B) shows the result of amylose resin. (C) shows the result of dextrin resin.
Figure 4B:
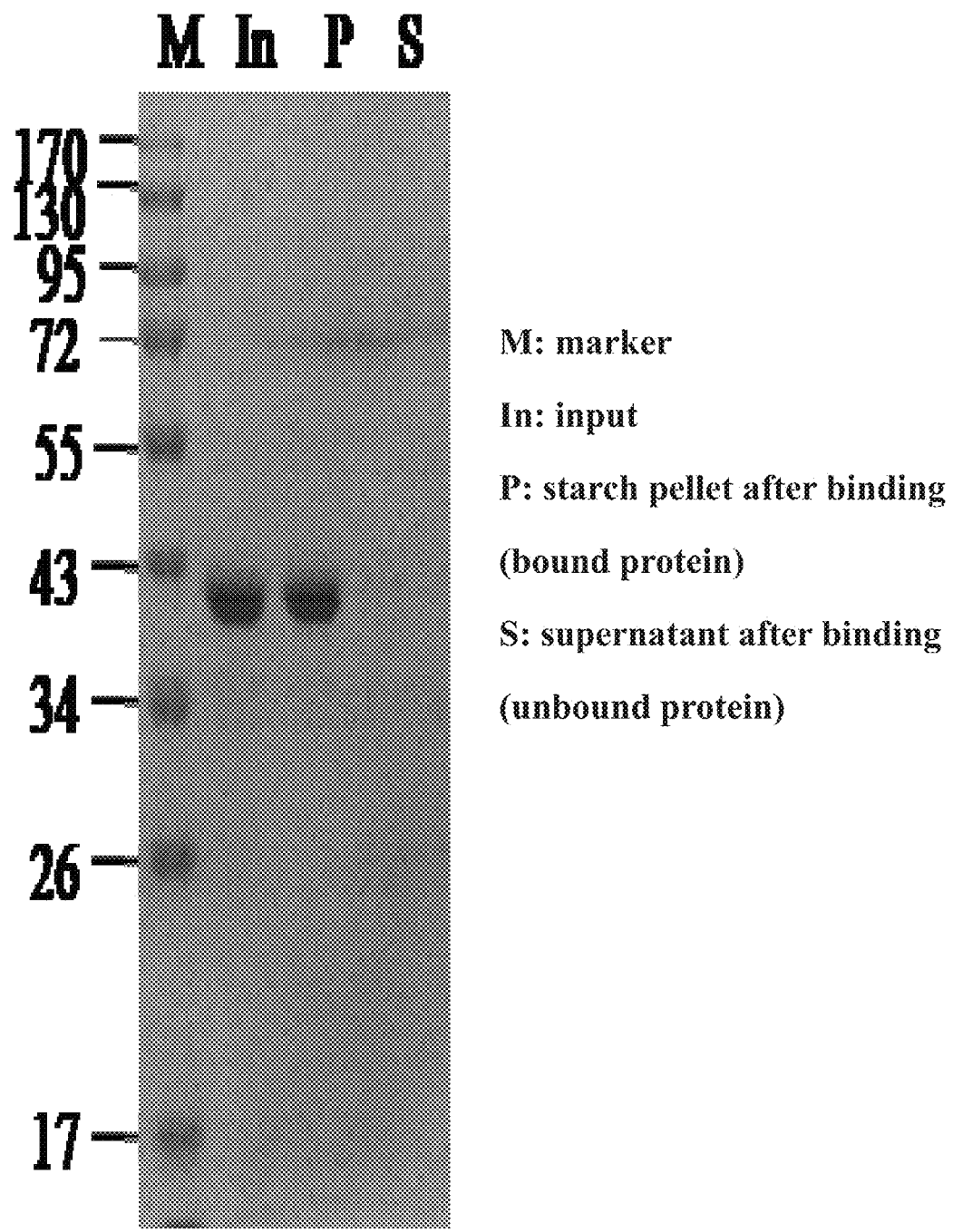
Figure 4C:
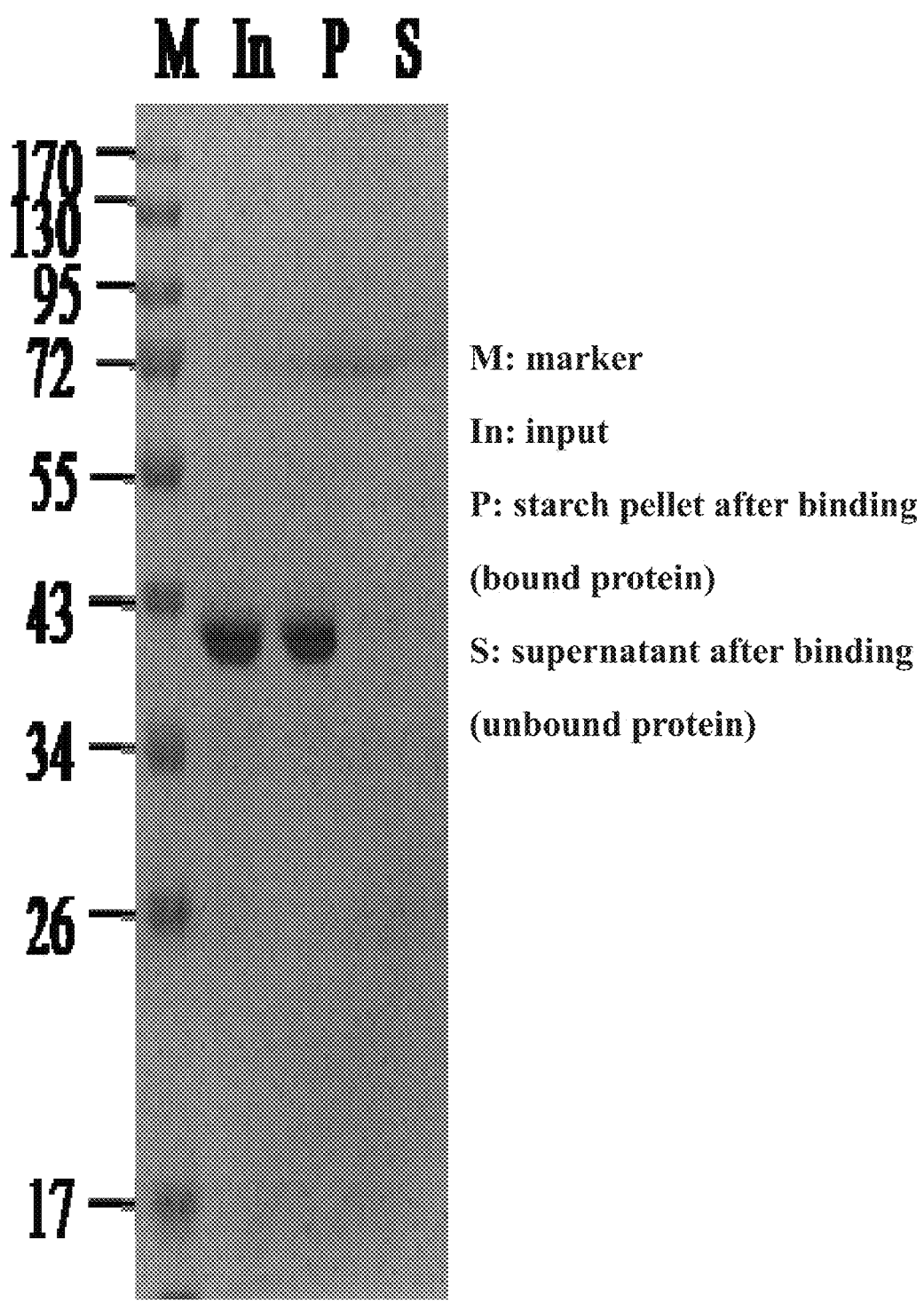

Two milligrams of prewashed amylopectin, amylose resin (Bio-Rad Laboratories Inc., Hercules, Calif., U.S.), dextrin resin (GE Healthcare, Waukesha, US) and sephadex (Sigma, Saint Louis, Mo., U.S.) were stirred with SBD-eGFP in binding buffer (50 mM NaOAc, pH 5.5) at a concentration of 0.3 mg/mL in a total volume of 200 μL. After incubation with stirring at 25° C. for 3 hr, the samples were centrifuged. The supernatant (unbound protein) and the resin pellets (bound protein) were then boiled and applied for SDS-PAGE. Results of the binding assay were showed in FIG. 4(A) to (C).

Binding Assay of SBD-eGFP to Alginate Beads

Figure 5:
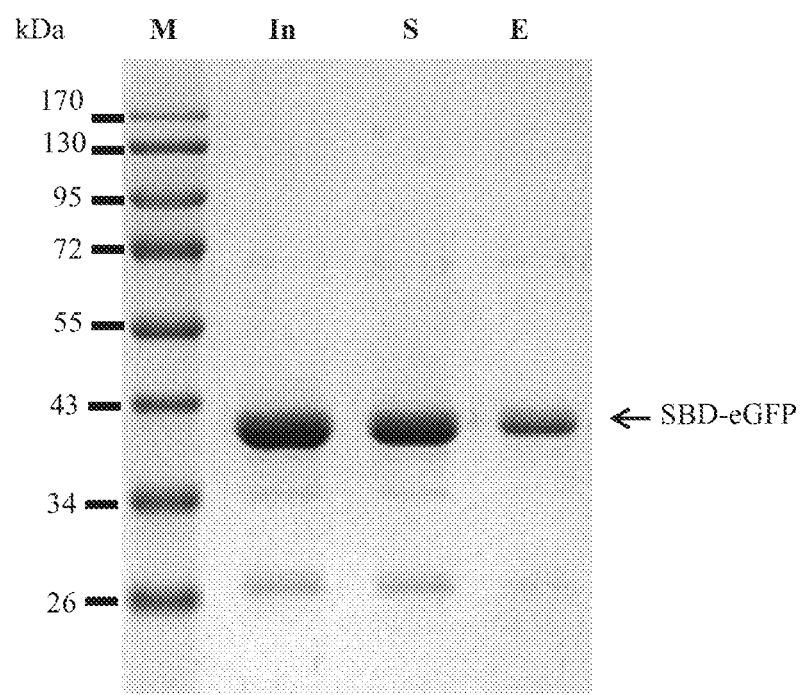
FIG. 5 shows the SDS-PAGE result of binding assay of SBD-eGFP to alginate beads.

Two hundred and fifty micro-liters of prewashed alginate beads were stirred with SBD-eGFP in binding buffer (50 mM NaOAc, pH 5.5) at a concentration of 0.6 mg/mL in a total volume of 1 mL. After incubation with stirring at 25° C. for 3 hr, the sample was centrifuged. The supernatant (unbound protein) was boiled and applied for SDS-PAGE. The alginate beads were then washed with 1 mL binding buffer. After that, 1 mL elution buffer (10 mM glycine/NaOH, pH 11) was added and stirred with the alginate beads at 25° C. for 30 min. The eluent and the remaining beads were also boiled and applied for SDS-PAGE. Results of the binding assay were showed in FIG. 5.

Example 4

Affinity-Tagged Purification and a "Clean-Cut" De-Tagging Process to Purify LZ8 (an Immune Regulator from Medical Fungus) or eGFP The SBP (SEQ ID NO: 1) gene was PCR amplified and fused to the C-termini of LZ8 (SEQ ID NO: 9) to form LZ8-eks-SBP or N-termini of eGFP (SEQ ID NO: 11) to form SBP-eks-eGFP with an enterokinase cleavage site (eks) between the SBP and target protein. The SBP gene (SEQ ID NO: 1) was PCR amplified and fused to the C-termini of enterokinase (SEQ ID NO: 12) to form EK-SBP. The LZ8-eks-SBP and EK-SBP were expressed in *P. pastoris* and SBP-eks-eGFP was expressed in insect cell.

Figure 6:
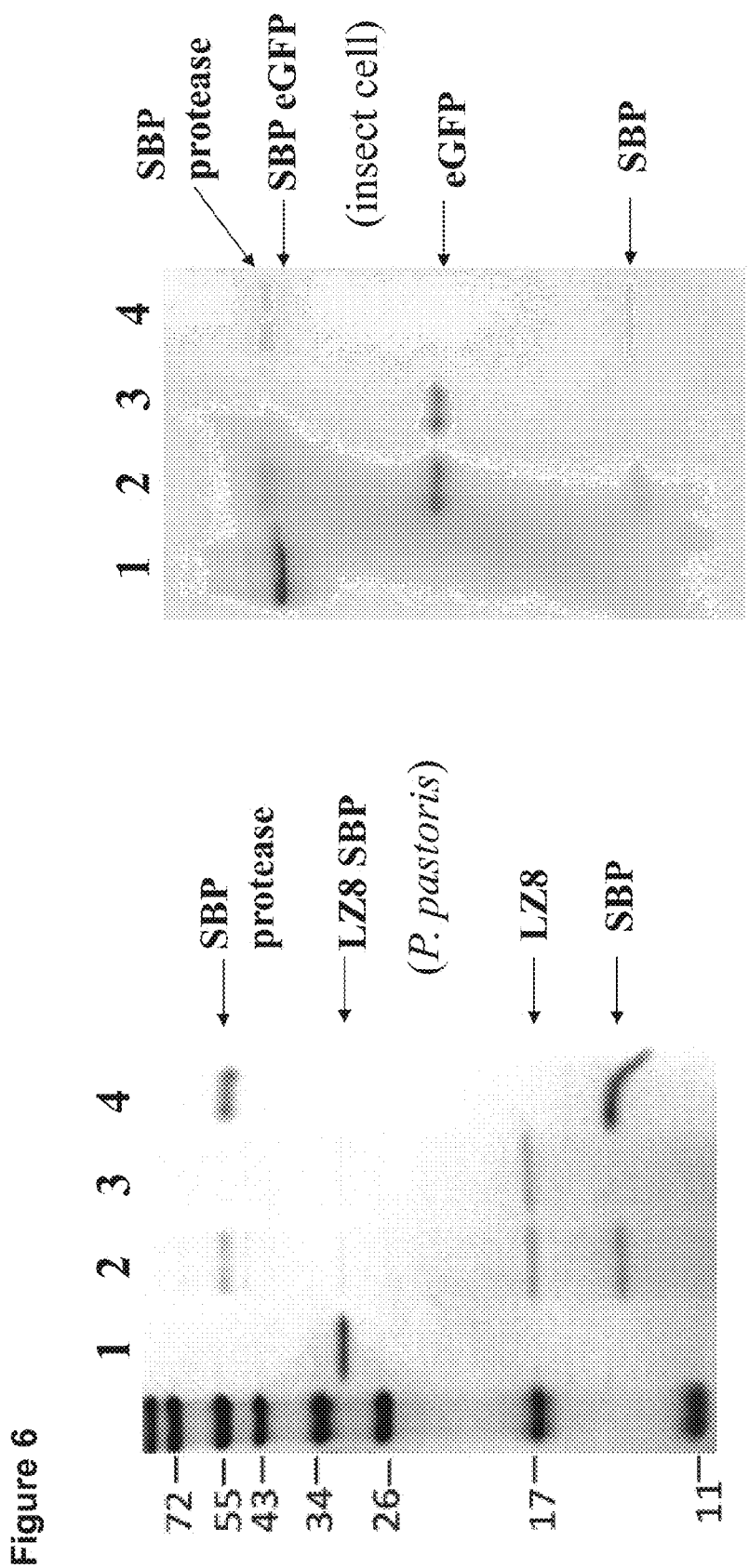
FIG. 6 shows the result of affinity-tagged purification and a "Clean-Cut" de-tagging process (LEFT: the result of LZ8; Right: the result of eGFP).

SBP-target proteins (LZ8-eks-SBP or SBP-eks-eGFP) were purified by $1^{st}$ starch-binding column, and then added SBP-protease (EK-SBP) to cleavage SBP-target proteins in 50 mM sodium acetate (pH5.5) at 37° C. for 3 hrs. Applied the mixture to $2^{nd}$ starch-binding column, flow-through were de-tagged target proteins (LZ8-eks or eGFP), after washing column with 50 mM sodium acetate (pH5.5), SBP-tagged residuals (Free SBP; EK-SBP and LZ8-eks-SBP SBP-eks-eGFP) were eluted by 10 mM Glycine/NaOH (pH11) buffer. The eluent was applied for SDS-PAGE and results were showed in FIG. 6 (LEFT: the result of LZ8; Right: the result of eGFP).

Example 5

Purification of Immunoglobulin by SBP-SpA Amylose Resin

Figure 7A:
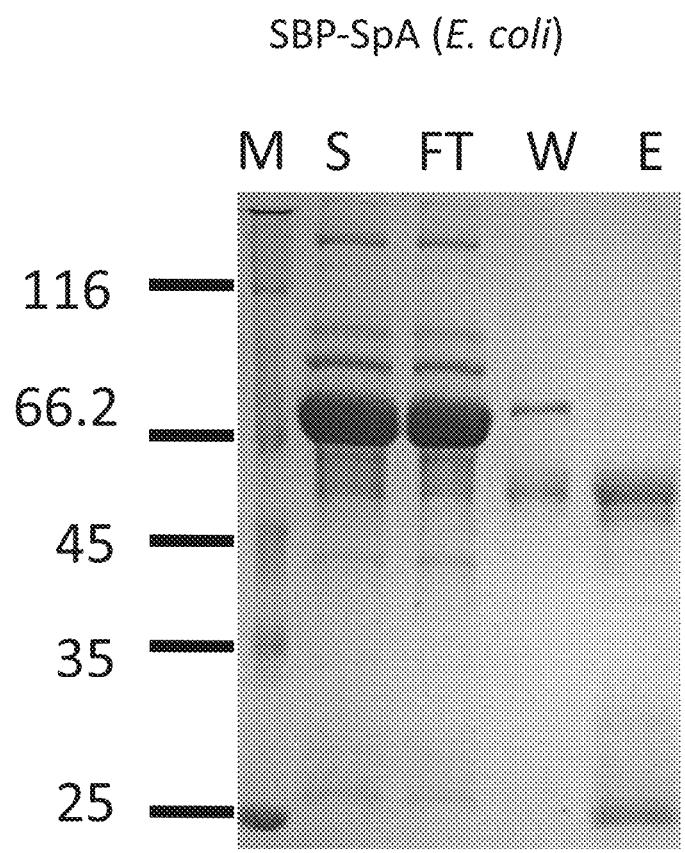
FIG. 7 shows the result of purification of immunoglobulin by SBP-SpA amylose resin. (A) shows the result of SBP-SpA purified from *Escherichia coli*. (B) shows the result of SBP-SpA purified from *Pichia*.
Figure 7B:
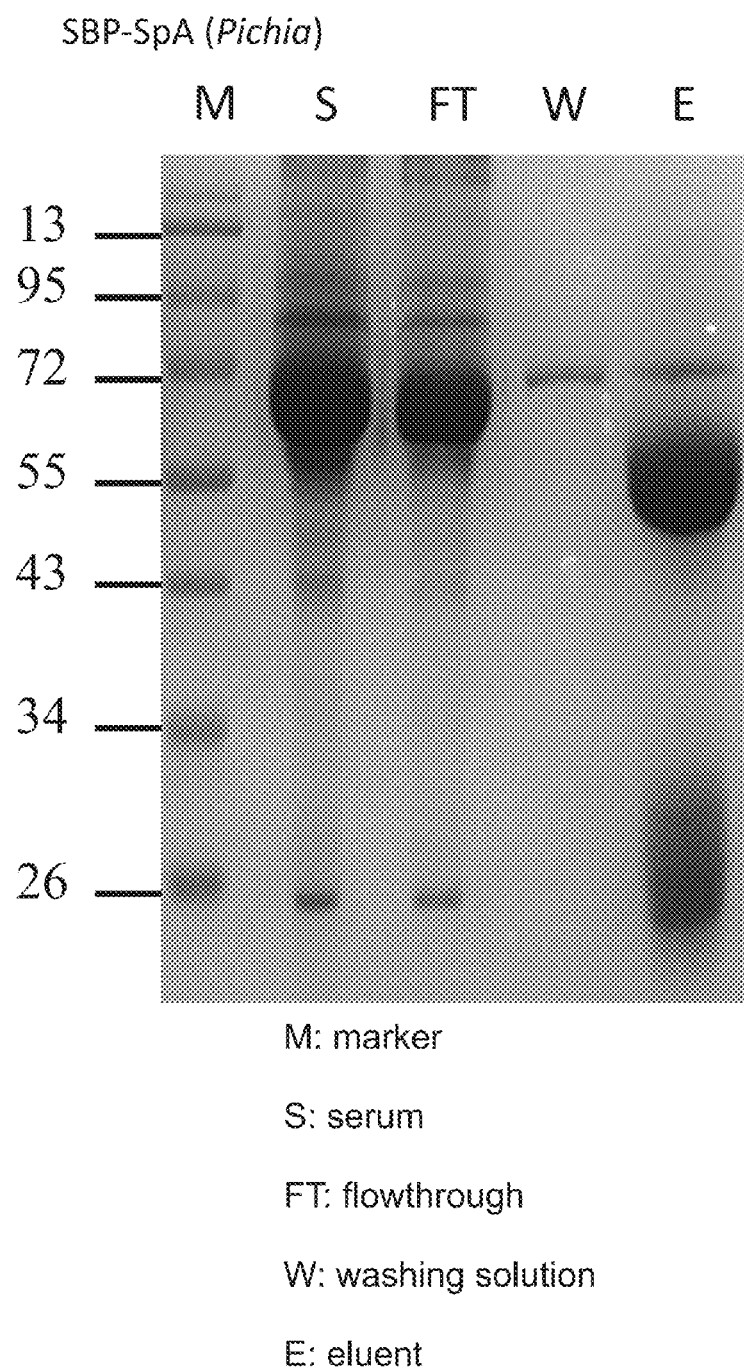

In order to purify IgG, SBP-SpA, a fusion protein of SBP and protein A, purified from *E. coli* or *Pichia* was immobilized on CNBr-activated agarose resin (Santa Cruz Biotechnology). Purification of IgG can be carried out by applying the sample to columns of packed SBP-SpA resin. Before the clarified serum applied to the resin, the serum sample should dilute 4 times in binding buffer (100 mM Tris+150 mM NaCl, pH 8.5). Applied the sample at a flow rate of 0.5-1 ml/min and then washed with 10 column volumes of binding buffer (100 mM Tris+150 mM NaCl, pH 8.5). Elution was carried out with 50 mM glycine/HCl, pH 2.5. As soon as the IgG had eluted, neutralized with 1M Tris, pH 8.0 and condensed 20 times. The eluent was applied for SDS-PAGE and results were showed in FIG. 7, wherein (A) showed the result of SBP-SpA purified from *E. coli* and (B) showed the result of SBP-SpA purified from *Pichia*.

The advantages may be summed up as following:

1. Extremely low production cost: For example, starch as affinity tag for Phytase (feed enzyme) in no de-tagged process cost less than 1.5 dollars per gram.

2. Clean-cut (tag-free) proteins: Clean-cut (tag-free) proteins might be produced by SBP-endoprotease de-tag system disclosed here.
3. High recovery rate: The recovery rate of disclosed system was pretty high and the rate was greater than 70%, optionally, the rate was greater than 90% in lab scale.
4. Very High fermentation titers: The fermentation titer of disclosed system was pretty high and the rate could be was greater than 10 g/l (i.e. *Pichia* expression system).
5. Successful expressed proteins in many hosts: Many proteins and enzymes were expressed in many hosts (e.g. *P. pastoris, S. cerevisiae, E. coli*, insect cells, yeast or the like).
6. Poor-expressed proteins can now be obtained: Poor-expressed proteins can now be obtained by using larger batch plus low-cost starch resin while still under budget.
7. Disposable protein purified and de-tag sub-system: There was a disposable protein purify and de-tag sub-system provided in the invention reducing possible contamination.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

What is claimed is:

1. A method for retaining an activity of a target protein in water, comprising:
    (a) fusing a starch binding protein (SBP) with the target protein to form a SBP-tagged recombinant protein;
    (b) expressing the SBP-tagged recombinant protein by an expression host;
    (c) combining the SBP-tagged recombinant protein with a SBP-binding matrix to form a complex; and
    (d) adding the complex of step (c) into water,
    wherein the SBP-binding matrix is selected from starch, alginate, amylopectin, dextrin resin or amylose resin, wherein the target protein is selected from phytase, lipase, xylanase, protease, agarase, cellulase, oxidase, dehydrogenase or immunoregulatory protein.

2. The method according to claim 1, wherein the expression host is a bacterium, a yeast, an insect cell or a mammalian cell.

3. The method according to claim 2, wherein the yeast is selected from *Pichia pastoris* or *Saccharomyces cerevisiae*.

4. The method according to claim 2, wherein the bacterium is selected from *E. coli, Bacillus subtilis* or *Brevibacillus choshinensis*.

5. The method according to claim 1, wherein the protease is selected from endoprotease, severe acute respiratory syndrome (SARS) protease or enterokinase.

6. The method according to claim 1, wherein the immunoregulatory protein is Ling Zhi 8 (LZ8).

7. The method according to claim 1, wherein the combination of the SBP-tagged protein with the SBP-binding matrix is used as an animal feed, a dietary supplement, a medical formulation or an immobilized catalyst.

* * * * *